US008430810B2

(12) United States Patent
Hassidov et al.

(10) Patent No.: US 8,430,810 B2
(45) Date of Patent: Apr. 30, 2013

(54) INFLATABLE BALLOON DEVICE AND APPLICATIONS

(75) Inventors: Noam Hassidov, Bustan Hagalil (IL); Daniel Glozman, Kefar Adummim (IL); Moshe Shoham, Hoshaya (IL)

(73) Assignee: Technion Research And Development Foundation, Ltd., Haifa (IL)

( * ) Notice: Subject to any disclaimer, the term of this patent is extended or adjusted under 35 U.S.C. 154(b) by 781 days.

(21) Appl. No.: 12/526,512

(22) PCT Filed: Feb. 12, 2008

(86) PCT No.: PCT/IL2008/000180
§ 371 (c)(1),
(2), (4) Date: Aug. 9, 2009

(87) PCT Pub. No.: WO2008/099389
PCT Pub. Date: Aug. 21, 2008

(65) Prior Publication Data
US 2010/0022947 A1    Jan. 28, 2010

Related U.S. Application Data

(60) Provisional application No. 60/900,698, filed on Feb. 12, 2007.

(51) Int. Cl.
*A61B 1/01* (2006.01)
*A61B 1/015* (2006.01)
(52) U.S. Cl.
USPC .......................................... 600/116; 600/139
(58) Field of Classification Search ........... 600/115–116
See application file for complete search history.

(56) References Cited

U.S. PATENT DOCUMENTS 2,855,934 A    10/1958  Daughaday
4,148,307 A *   4/1979  Utsugi ......................... 600/116
(Continued)

FOREIGN PATENT DOCUMENTS
DE    3425483 A1    1/1986
DE    19708001      8/1998
(Continued)

OTHER PUBLICATIONS

European Supplementary Search Report dated Oct. 5, 2011 in corresponding European Application No. 08710180.4.

(Continued)

*Primary Examiner* — Clayton E Laballe
*Assistant Examiner* — Leon W Rhodes, Jr.
(74) *Attorney, Agent, or Firm* — Daniel Feigelson

(57) ABSTRACT

A self-propelled device for locomotion through a lumen, comprising a set of serially arranged inflatable chambers, and incorporating a number of novel aspects. To enable easy insertion and use, the rigidity of the device is increased by means of rigid inserts in the balloons, or by use of stiff springs between segments. The working channel can be attached to the distal chamber of the device, such that it is pulled from the leading end of the device during inflation, rather than being pulled from the trailing end of the device during deflation. Lumen wall inspection or treatment facilities are enabled by means of a camera or treatment arm mounted between two distally positioned balloons, the device is able to provide observation capabilities to the lumen wall, yet without becoming excessively dirty by exposure to the front end of the device, as in prior art camera units.

19 Claims, 32 Drawing Sheets

U.S. PATENT DOCUMENTS

| | | | |
|---|---|---|---|
| 4,176,662 A | 12/1979 | Frazer | |
| 4,372,161 A | 2/1983 | De Buda et al. | |
| 4,676,228 A | 6/1987 | Krasner et al. | |
| 4,838,859 A | 6/1989 | Strassmann | |
| 5,014,515 A * | 5/1991 | Krauter | 60/581 |
| 5,090,259 A | 2/1992 | Shishido et al. | |
| 5,144,848 A | 9/1992 | Uenishi | |
| 5,337,732 A | 8/1994 | Grundfest et al. | |
| 5,364,353 A | 11/1994 | Corfitsen et al. | |
| 5,662,587 A * | 9/1997 | Grundfest et al. | 600/114 |
| 5,906,591 A | 5/1999 | Dario et al. | |
| 6,007,482 A | 12/1999 | Madni et al. | |
| 6,517,477 B1 | 2/2003 | Wendlandt | |
| 6,616,629 B1 | 9/2003 | Verin et al. | |
| 6,702,735 B2 | 3/2004 | Kelly et al. | |
| 6,764,441 B2 | 7/2004 | Chiel et al. | |
| 6,824,510 B2 | 11/2004 | Kim et al. | |
| 6,939,291 B2 | 9/2005 | Phee Soo Jay et al. | |
| 7,264,588 B2 * | 9/2007 | Voloshin et al. | 600/115 |
| 2003/0065250 A1 | 4/2003 | Chiel et al. | |
| 2005/0033343 A1 | 2/2005 | Chermoni | |
| 2005/0197531 A1 | 9/2005 | Cabiri et al. | |
| 2007/0015965 A1 | 1/2007 | Cox | |
| 2008/0091068 A1 * | 4/2008 | Terliuc | 600/116 |

FOREIGN PATENT DOCUMENTS

| | | |
|---|---|---|
| JP | 01-216239 | 8/1989 |
| JP | PD H03-231623 A | 10/1991 |
| JP | PD 4-236964 A | 8/1992 |
| JP | PD H07-116112 A | 5/1995 |
| JP | PD 2006-141935 A | 6/2006 |
| WO | WO 2007/017876 | 2/2007 |

OTHER PUBLICATIONS

P. Dario et al, "Development and in vitro testing . . . for computer assisted colonoscopy", Computer Aided Surgery, vol. 4, pp. 1-14, 1999, Wiley.

Byungkyu K et al, "A Locomotive Mechanism for a Robotic Colonoscope", Proceedings IEEE/RSJ Intl. Confrc Robots & Systems ;2002, pp. 1373-1378.

J. Dietrich et al, "Development of a peristaltically actuated device..", Micro-and Nanostructures of Biological Systems, Halle,Shaker-Verlag,69-88, 2004.

PCT Int'l Search Report and Written Examination of the ISA, mailed Nov. 12, 2008 in PCT/IL08/00180.

* cited by examiner

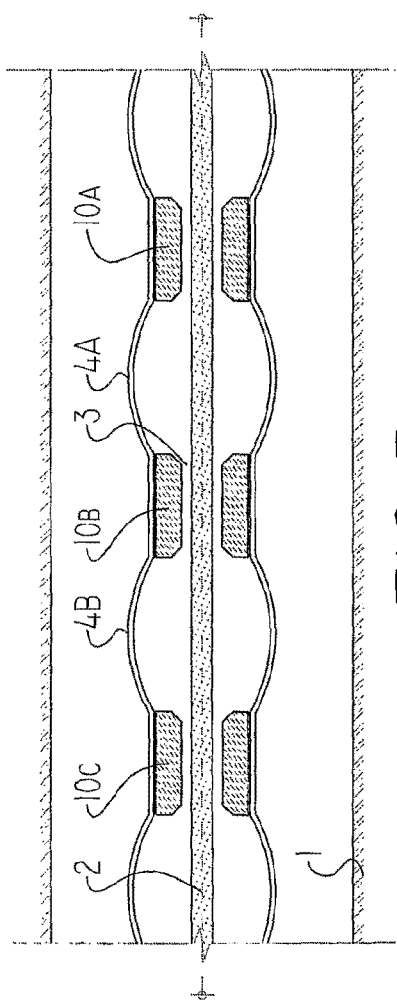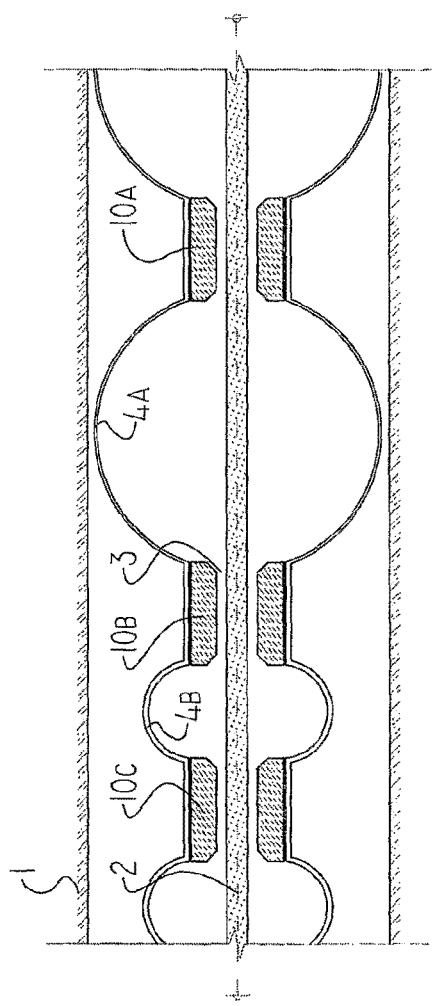

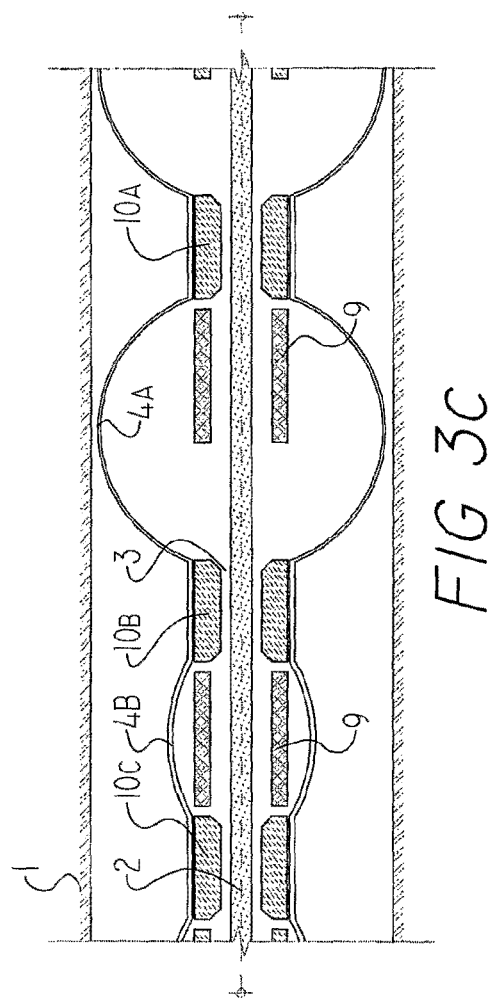

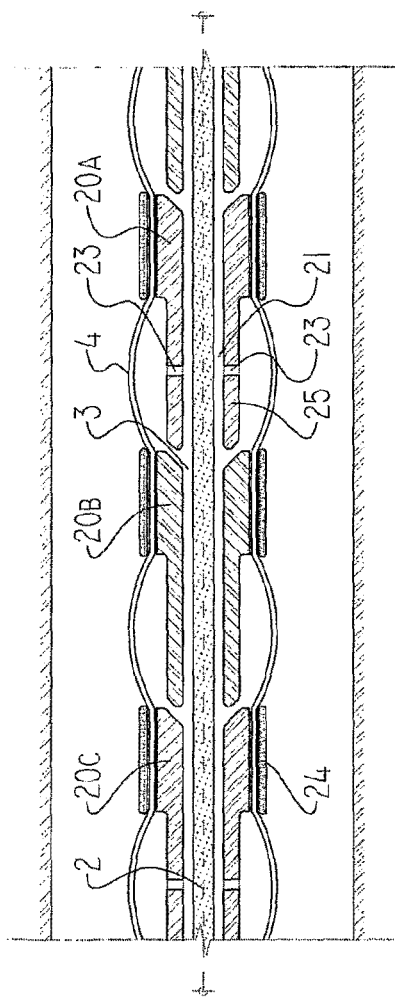
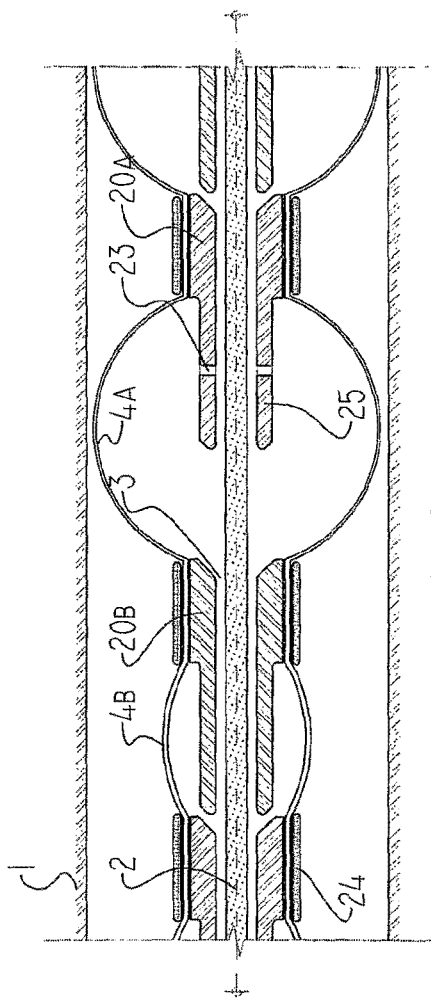

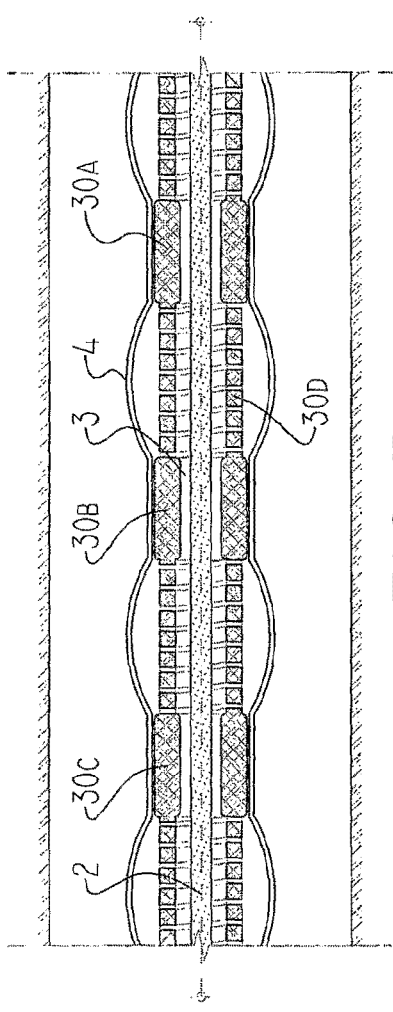
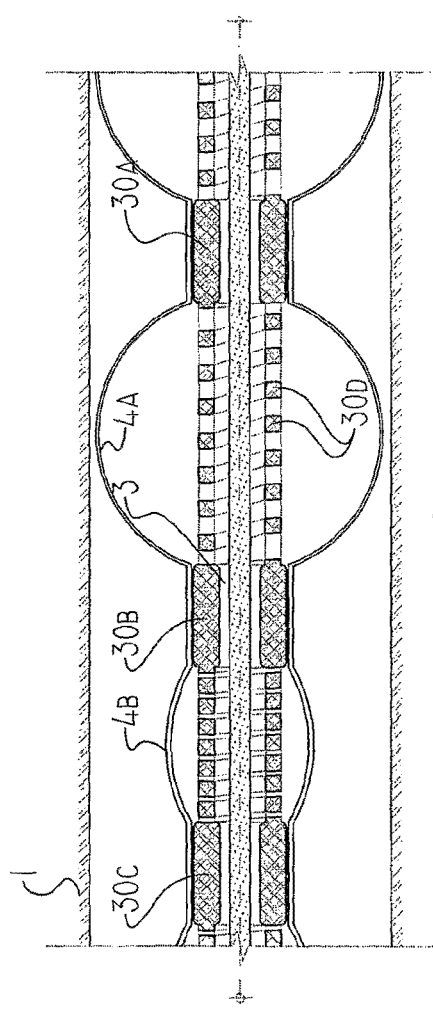

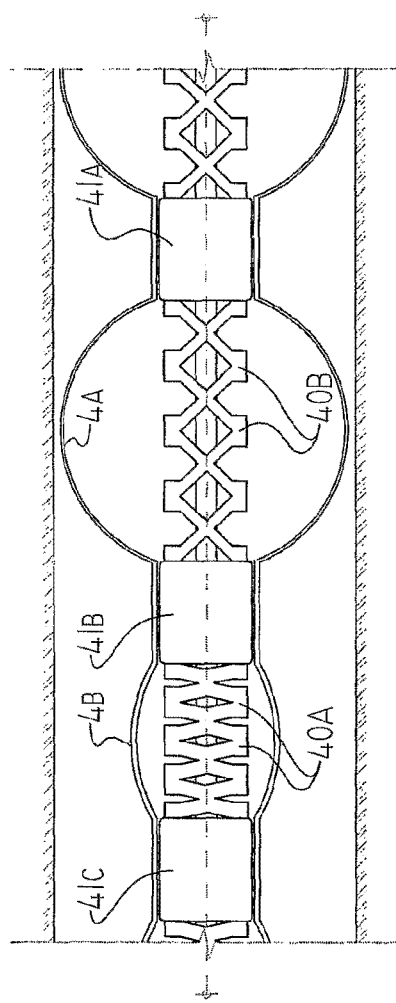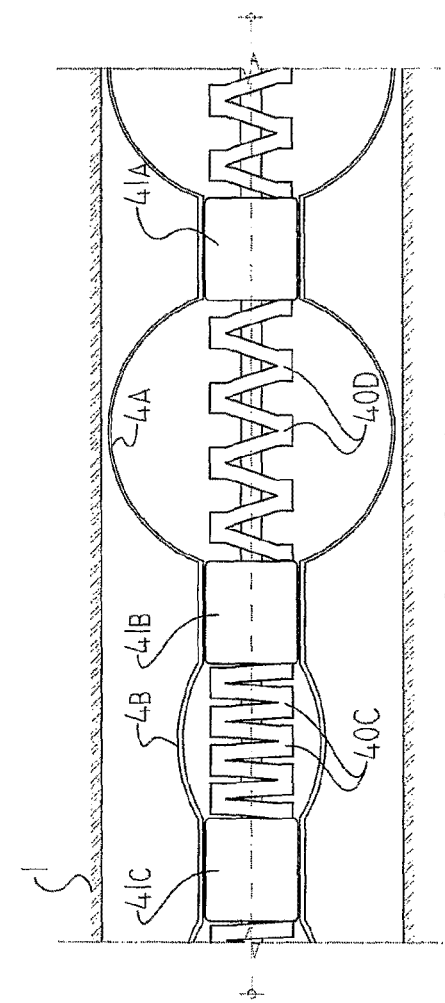

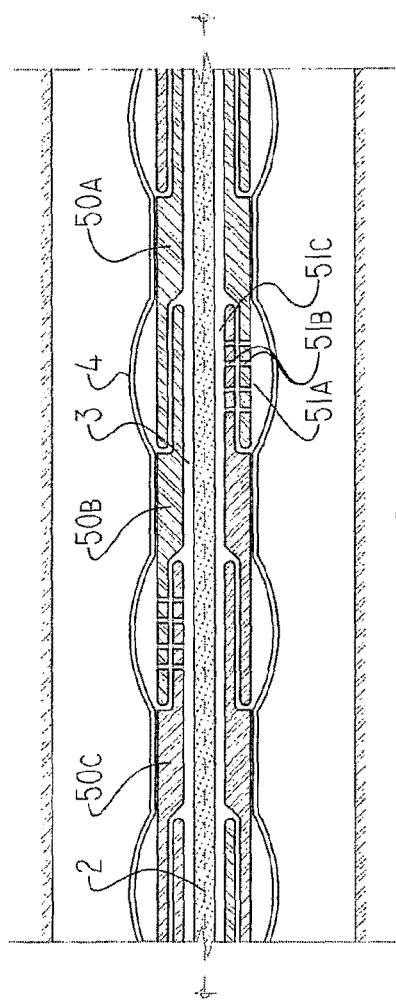
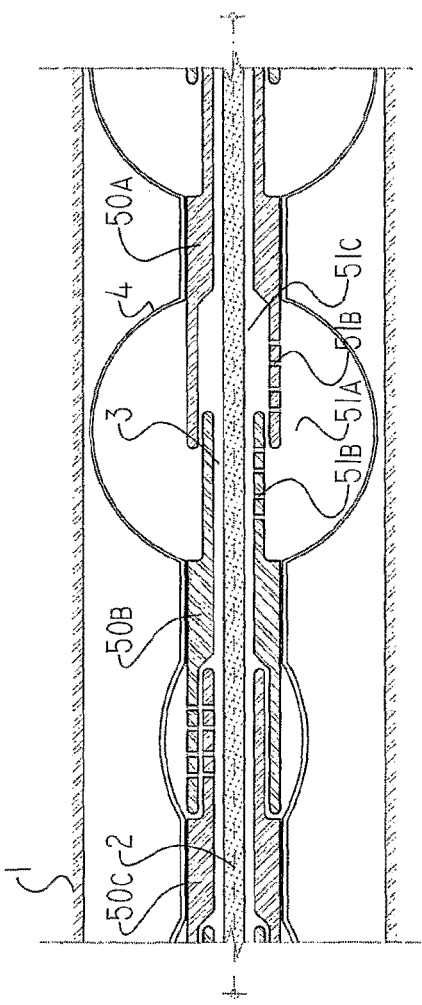
FIG 7A
FIG 7B

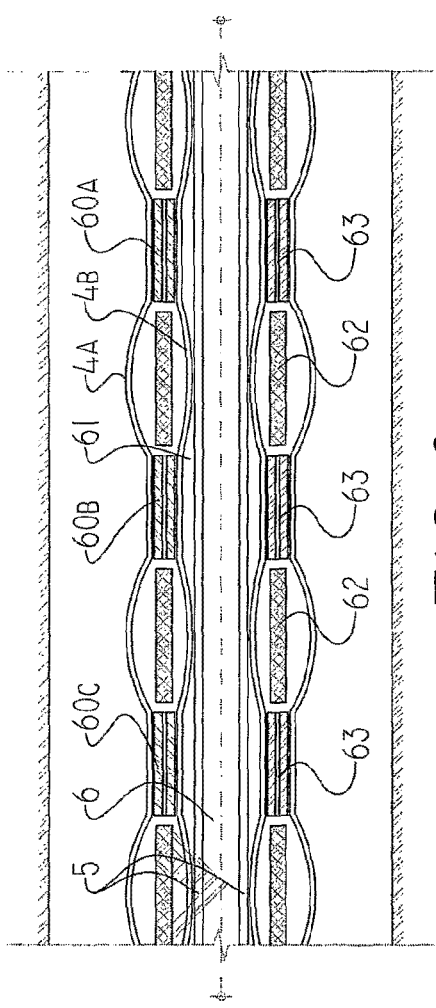
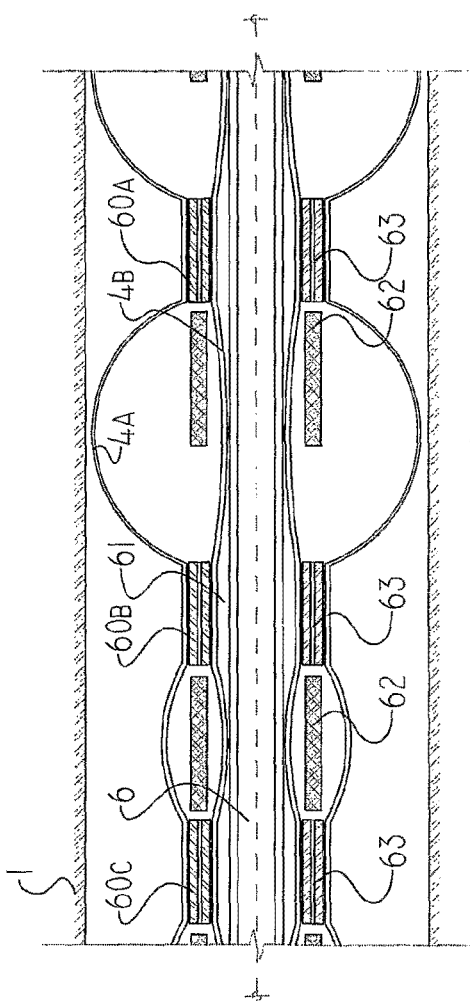

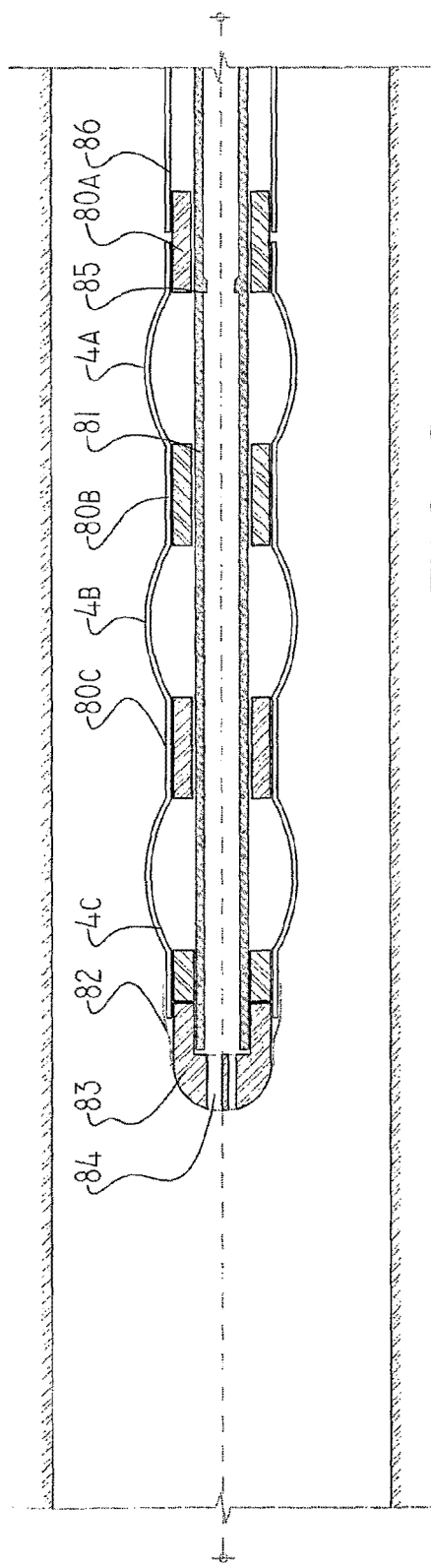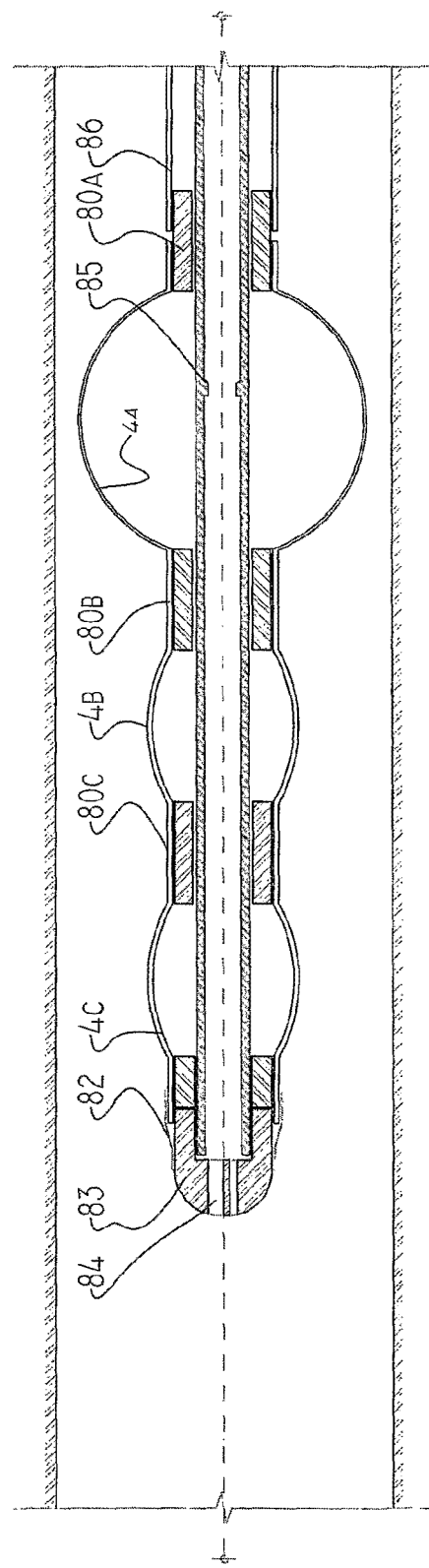

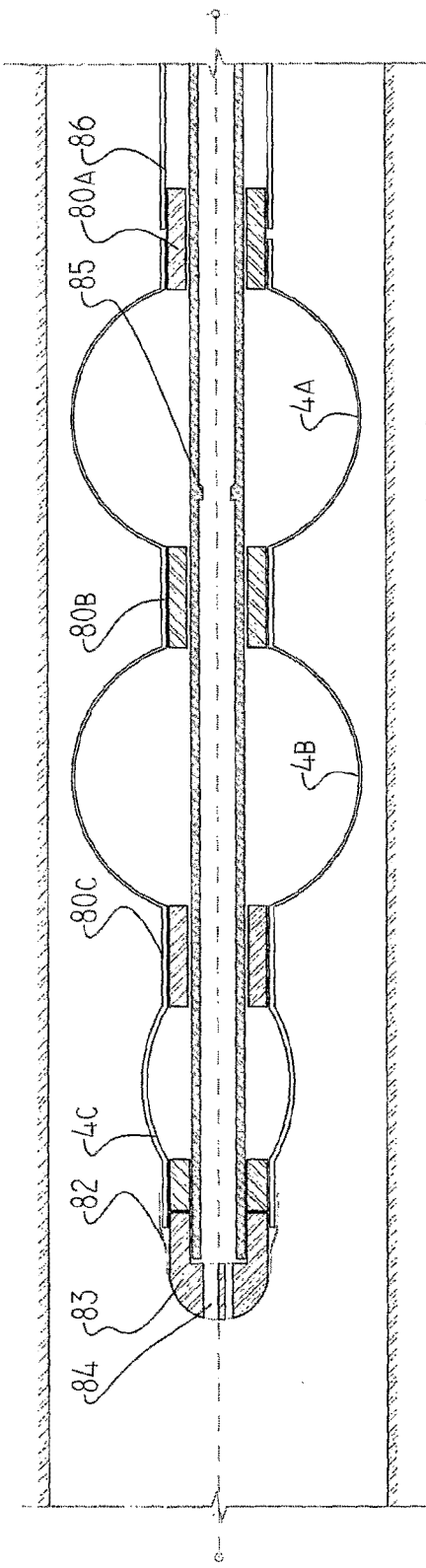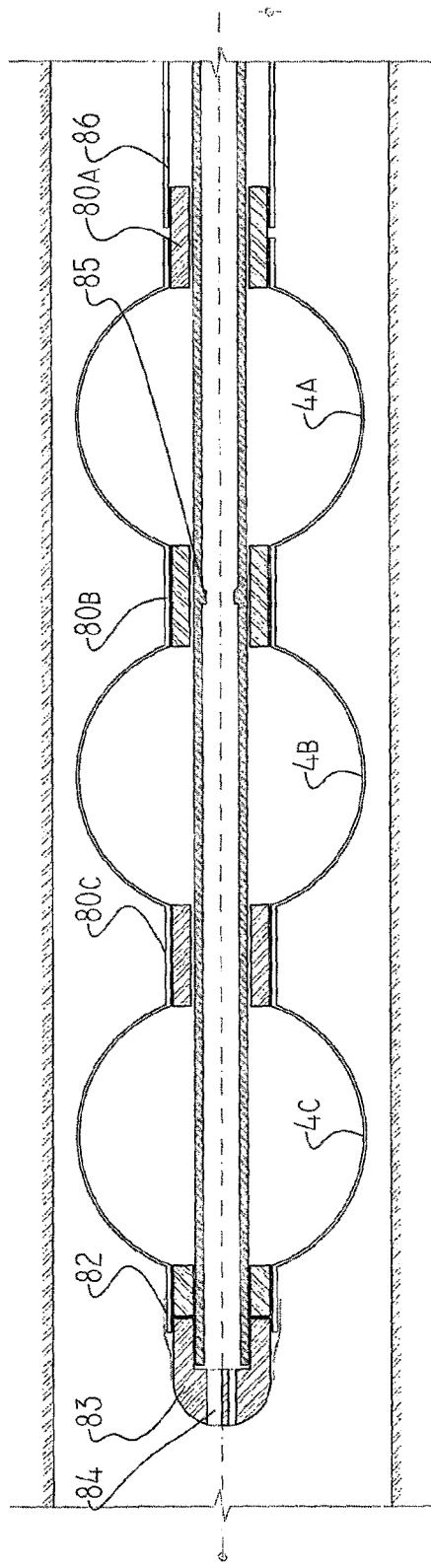

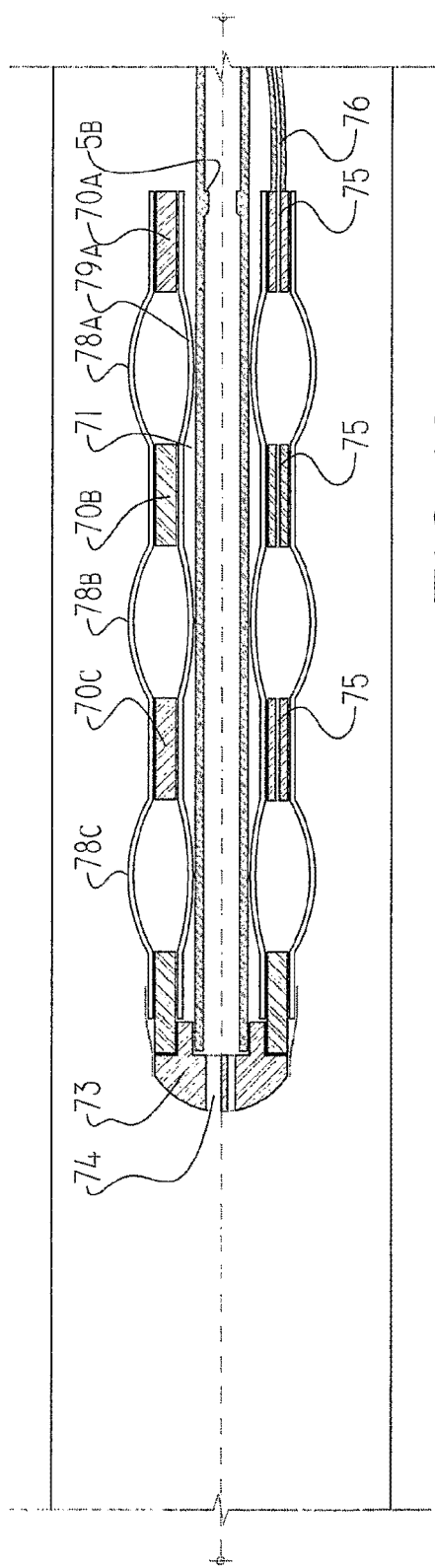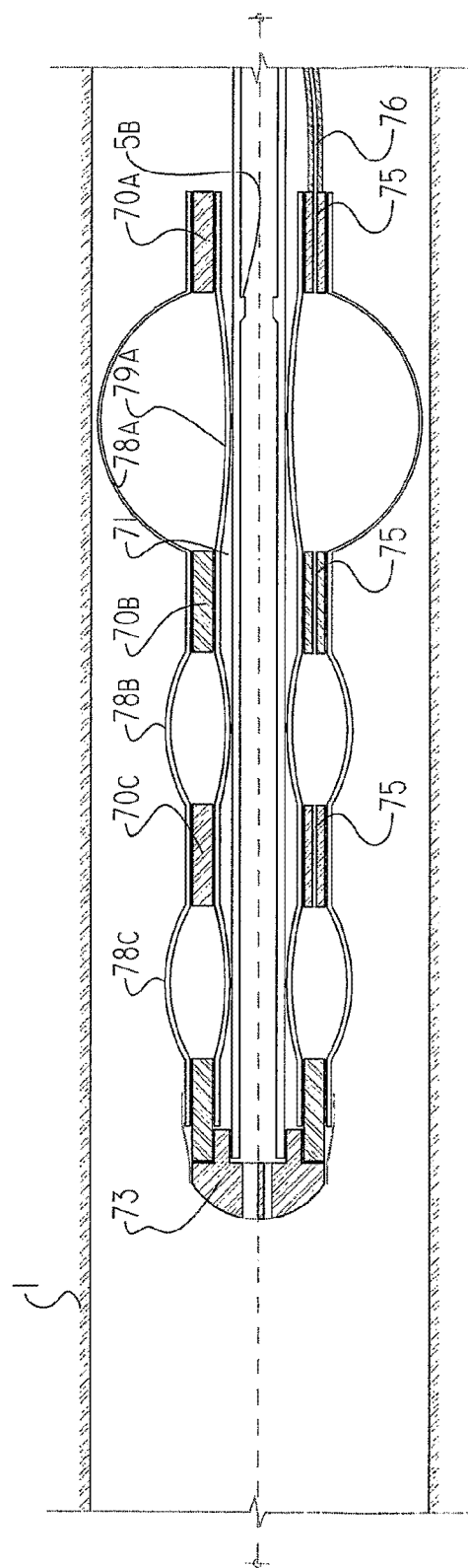
FIG 10A
FIG 10B

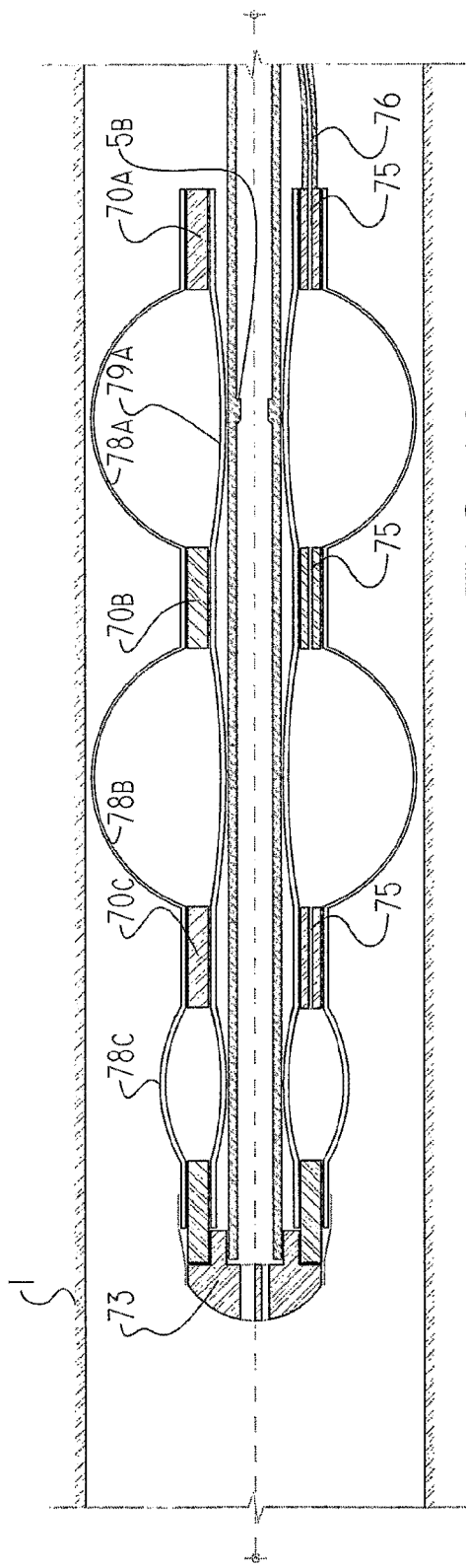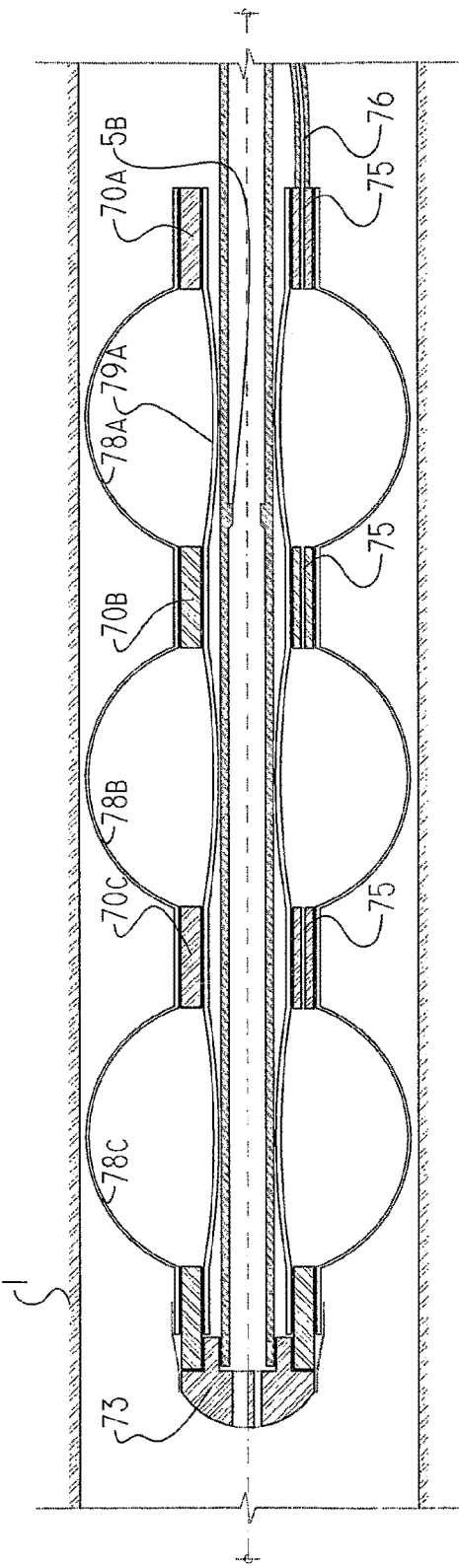

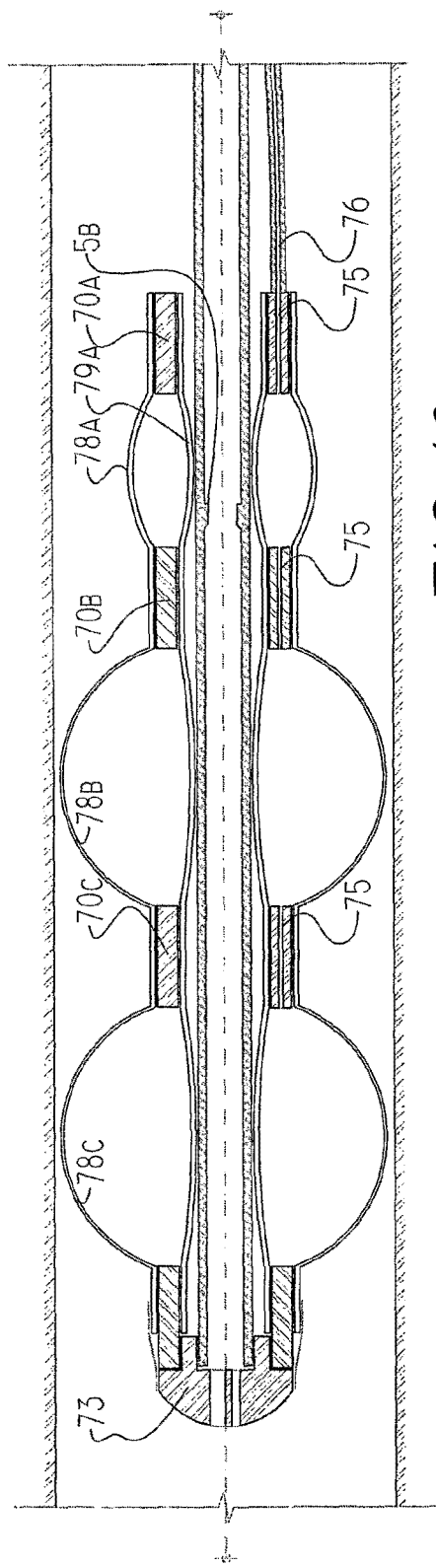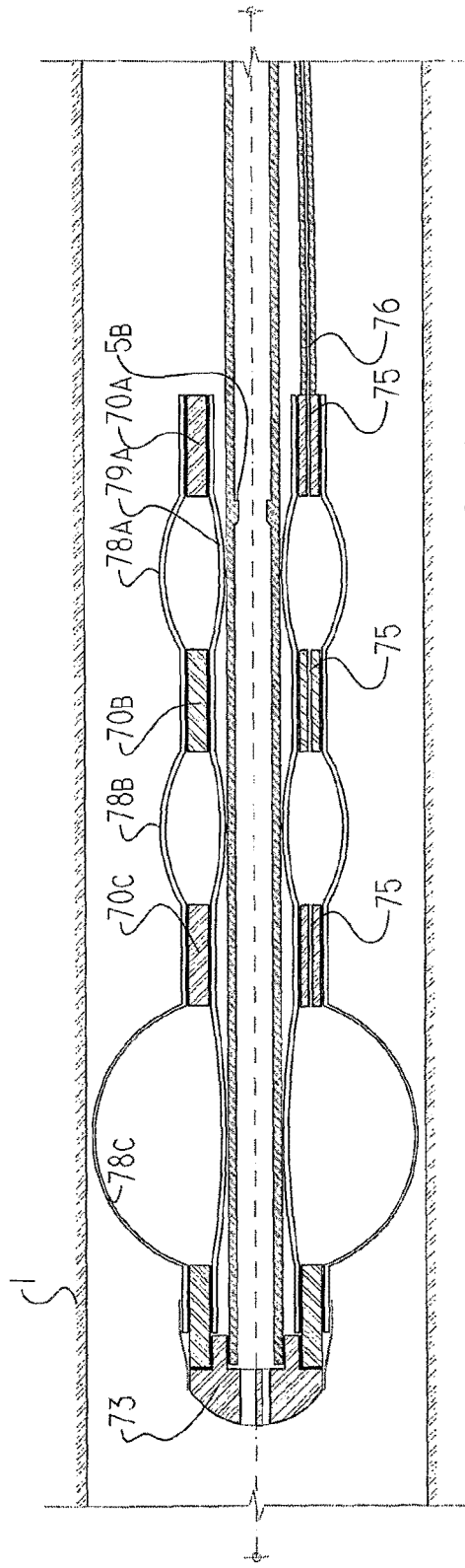

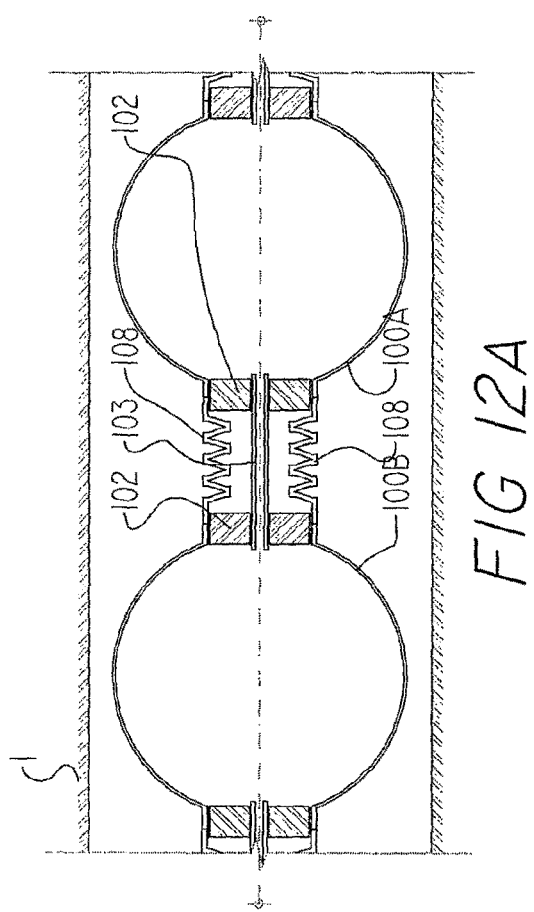

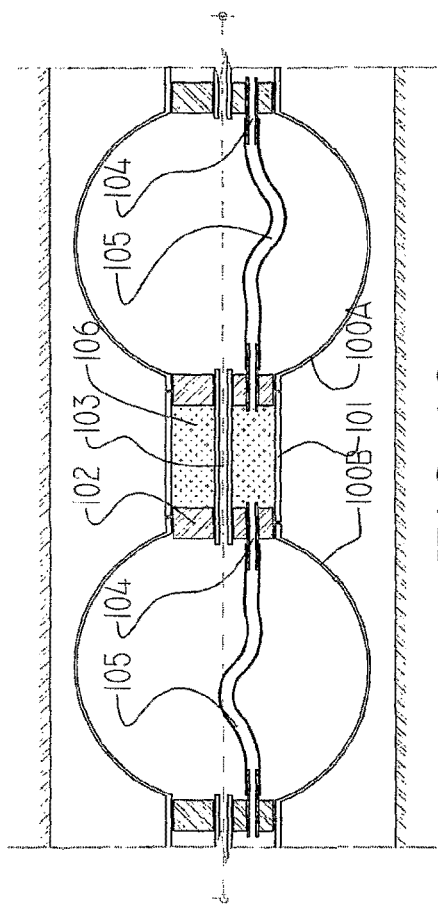
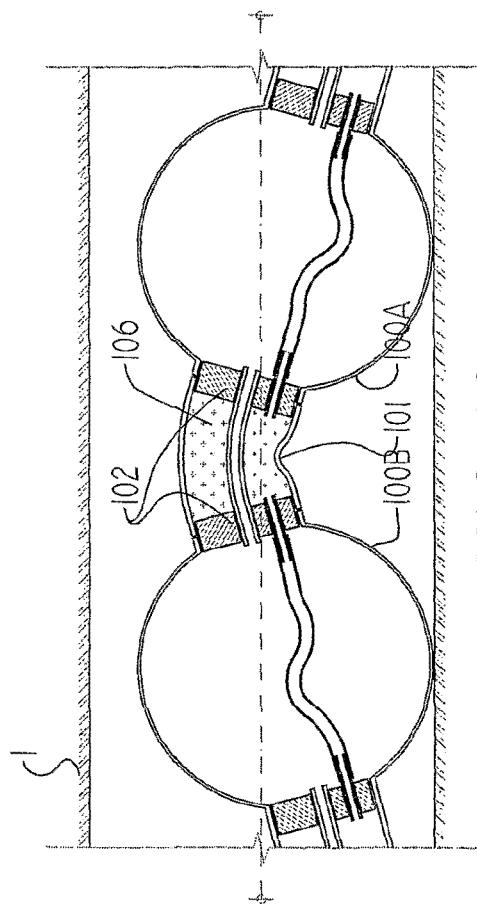
FIG 12B
FIG 12C

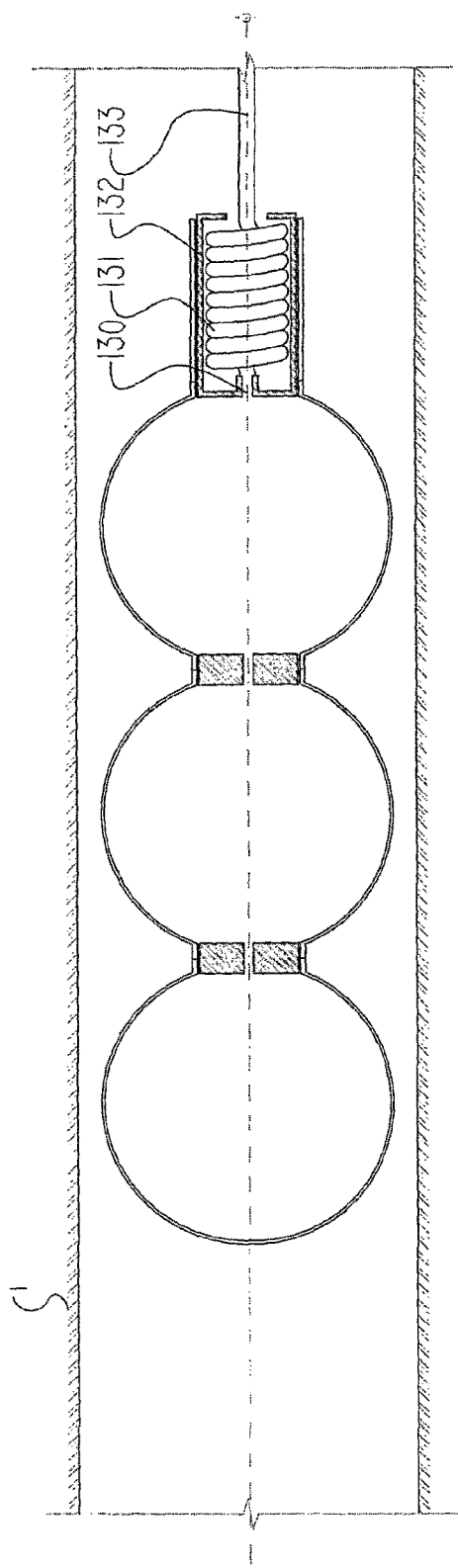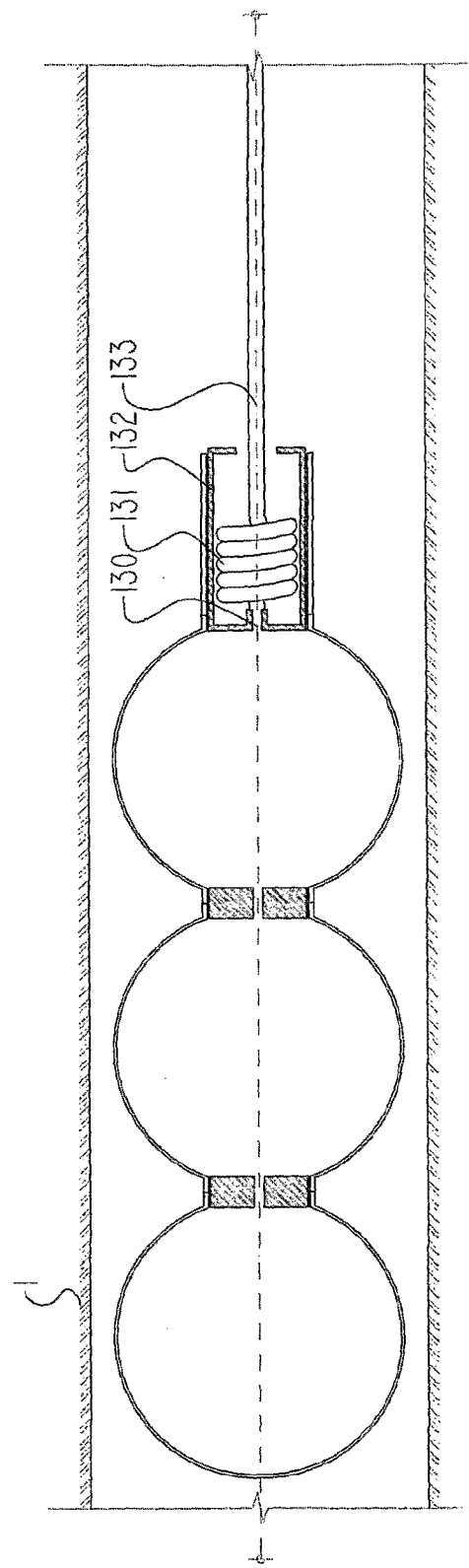

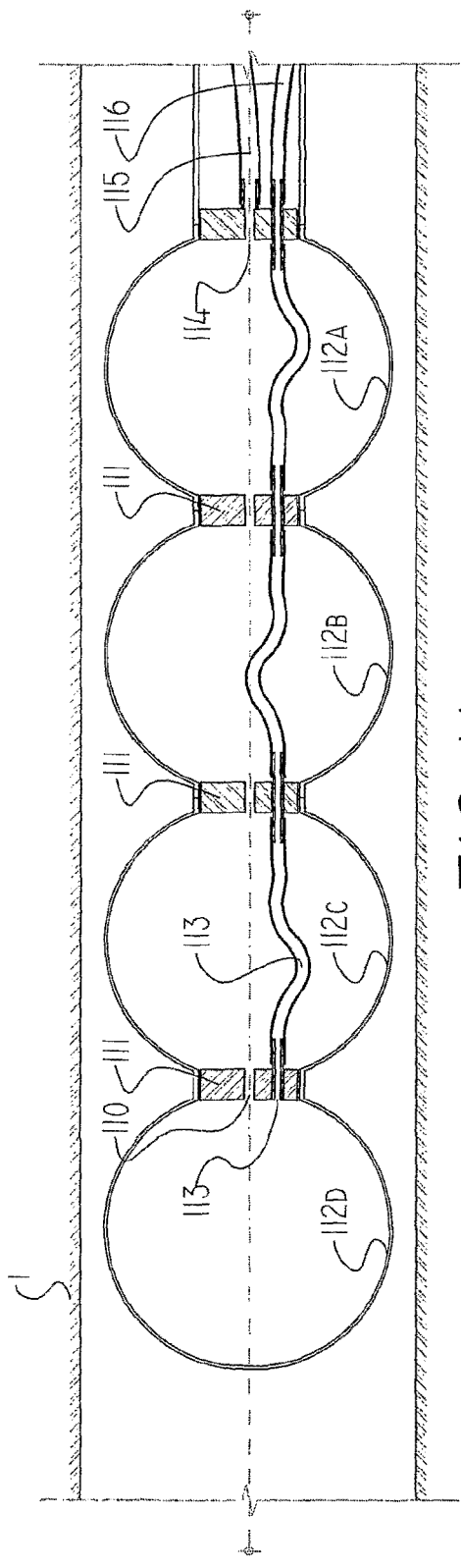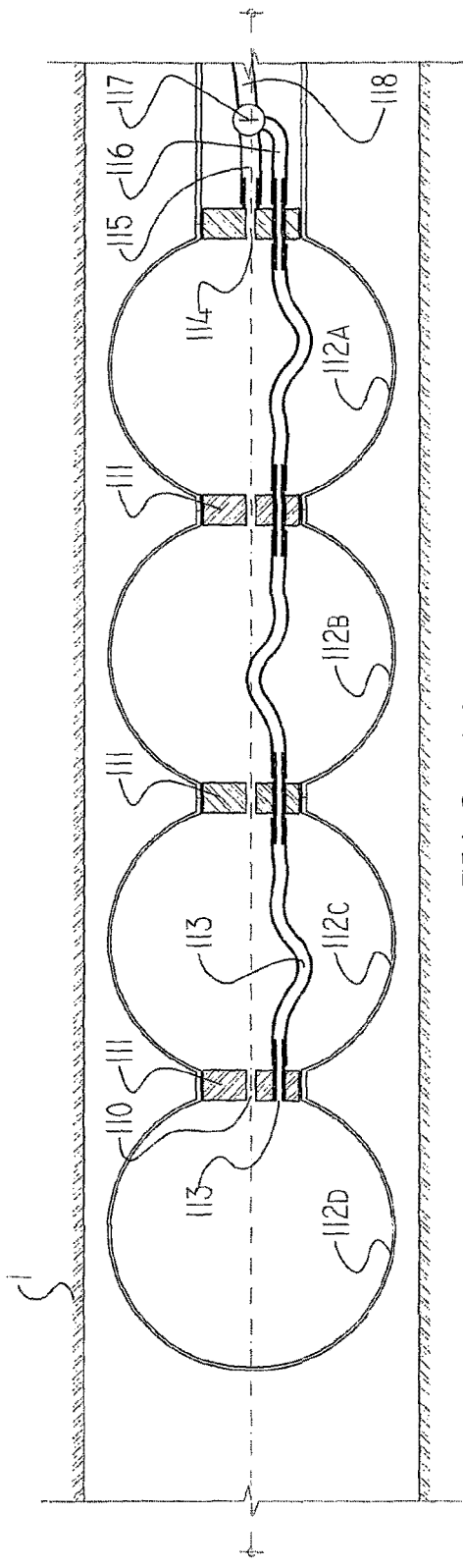

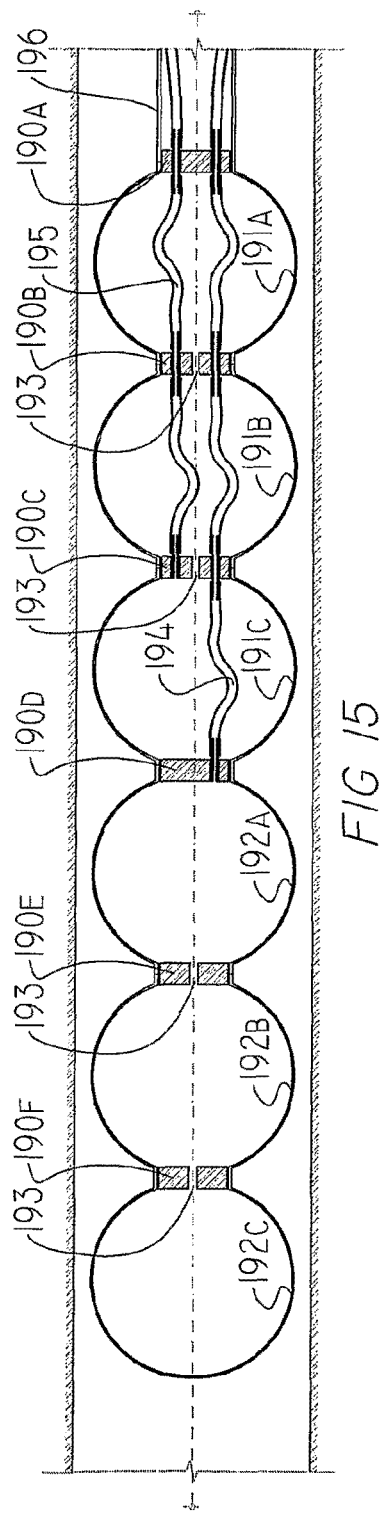

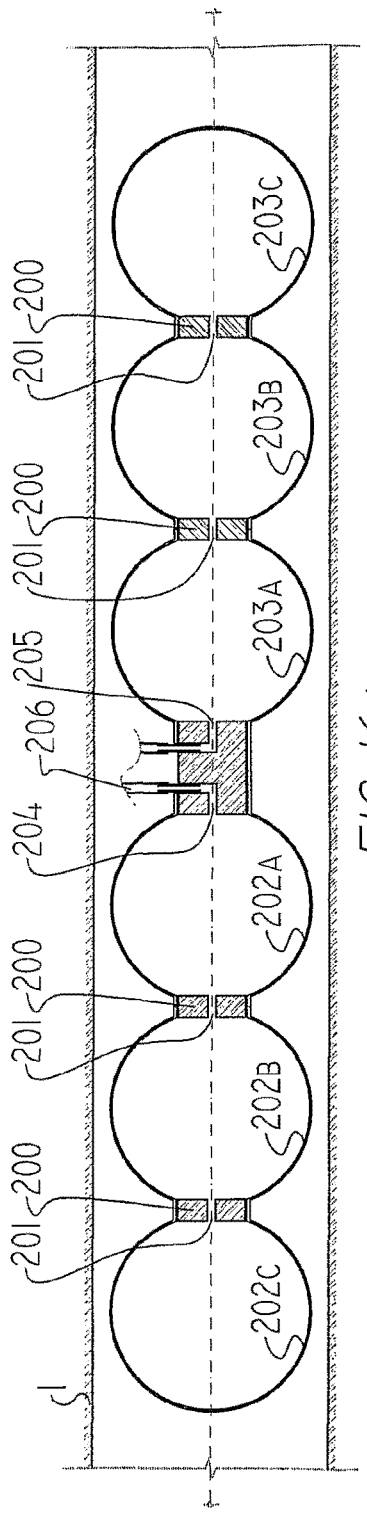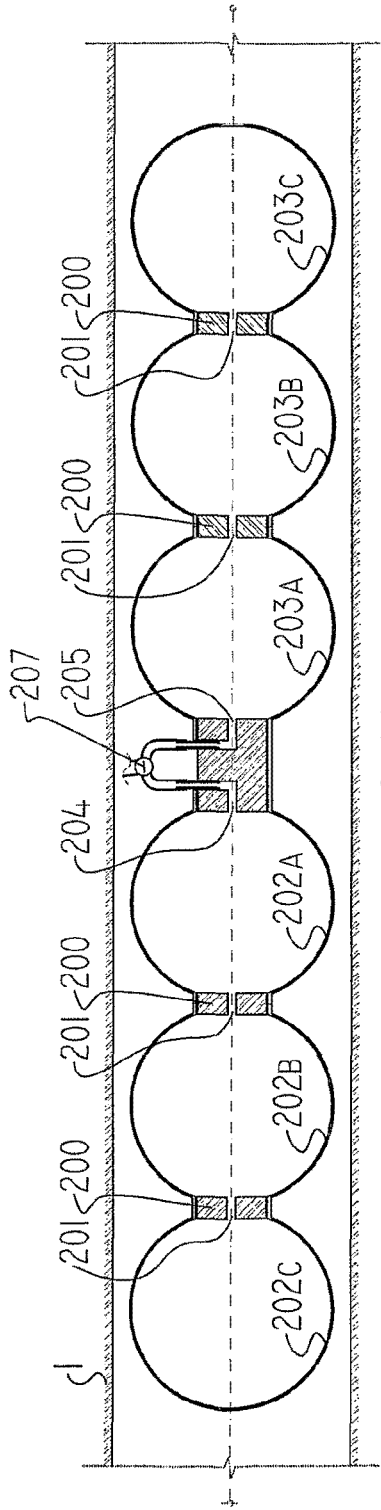

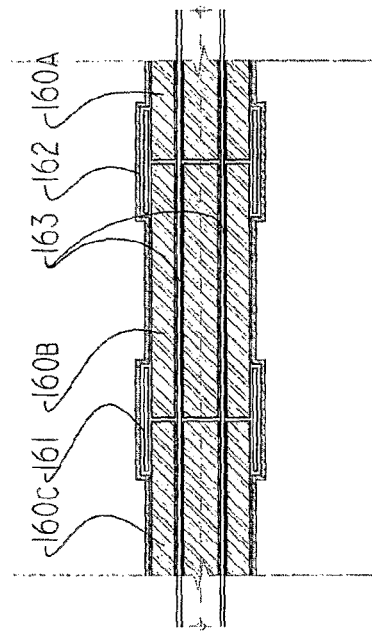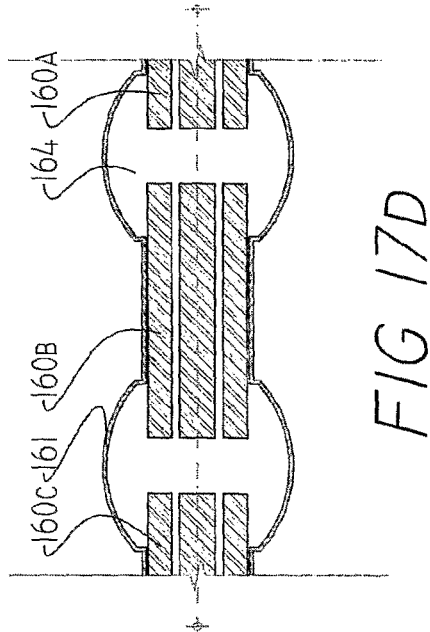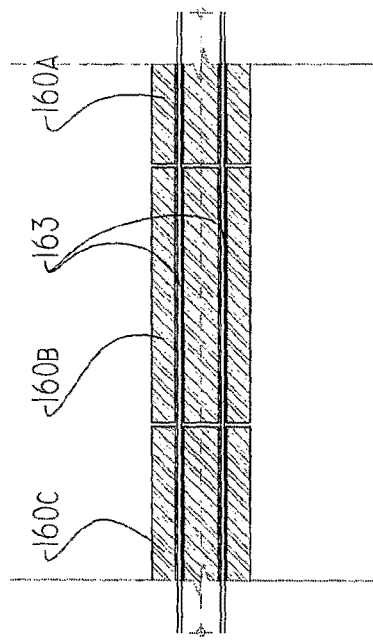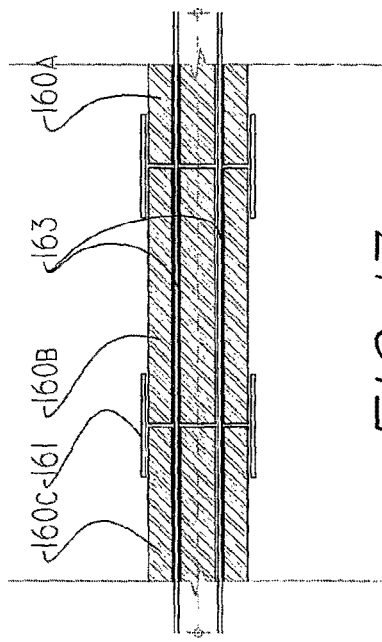

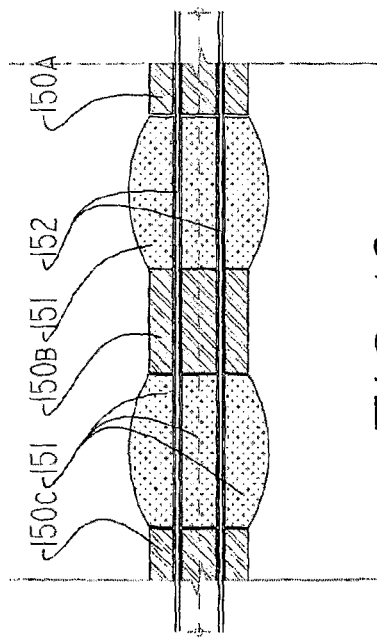
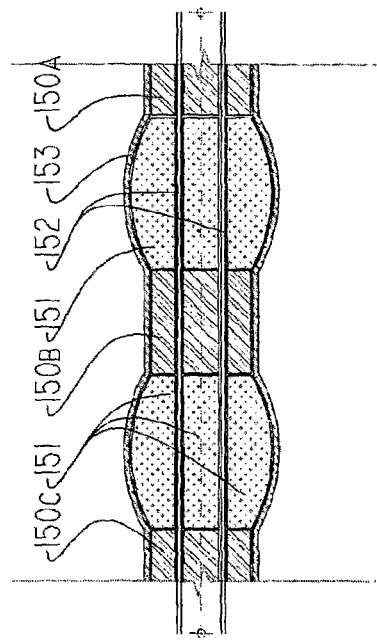
FIG 18A
FIG 18B
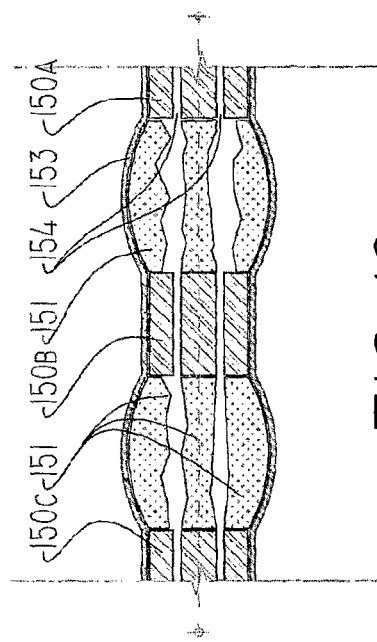
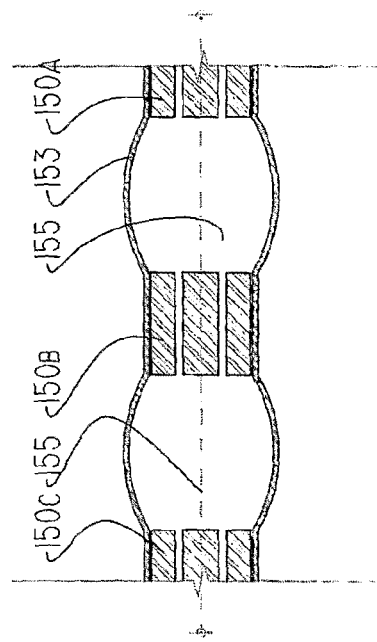
FIG 18C
FIG 18D

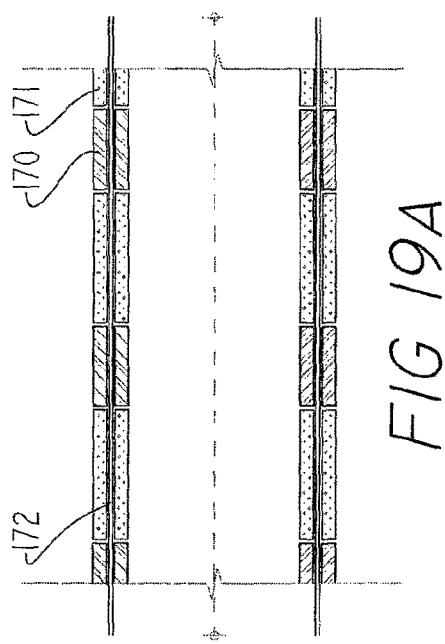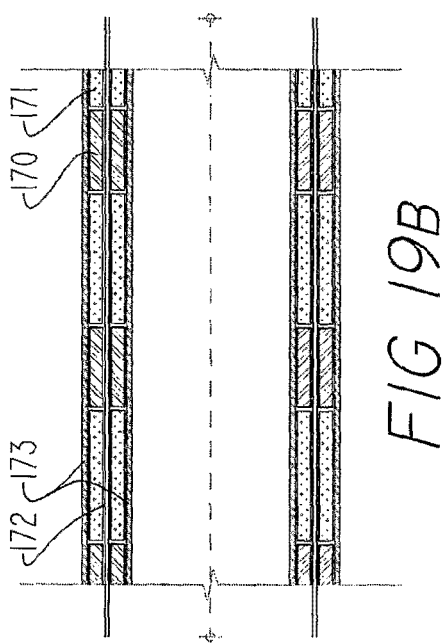

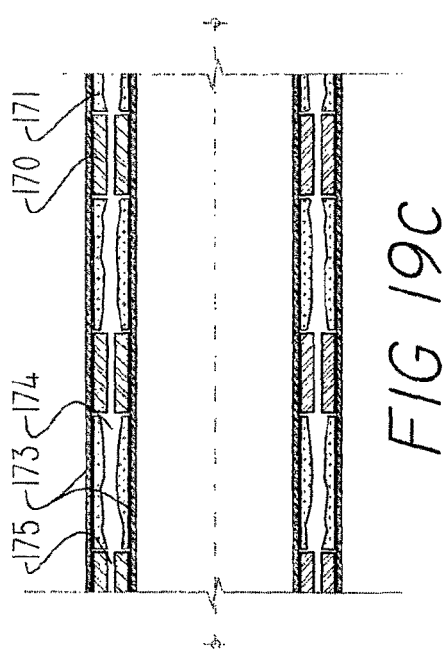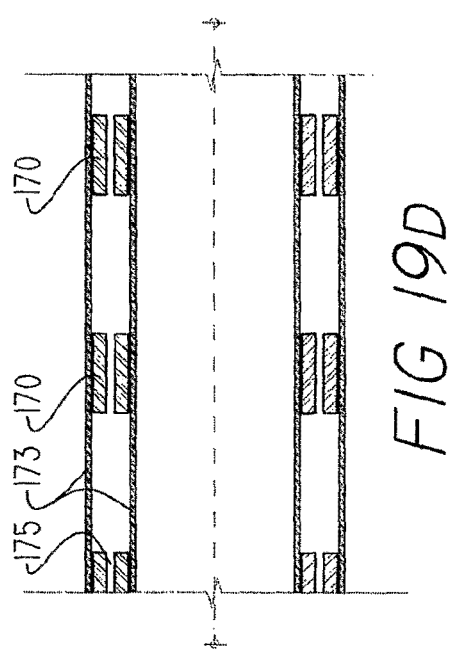

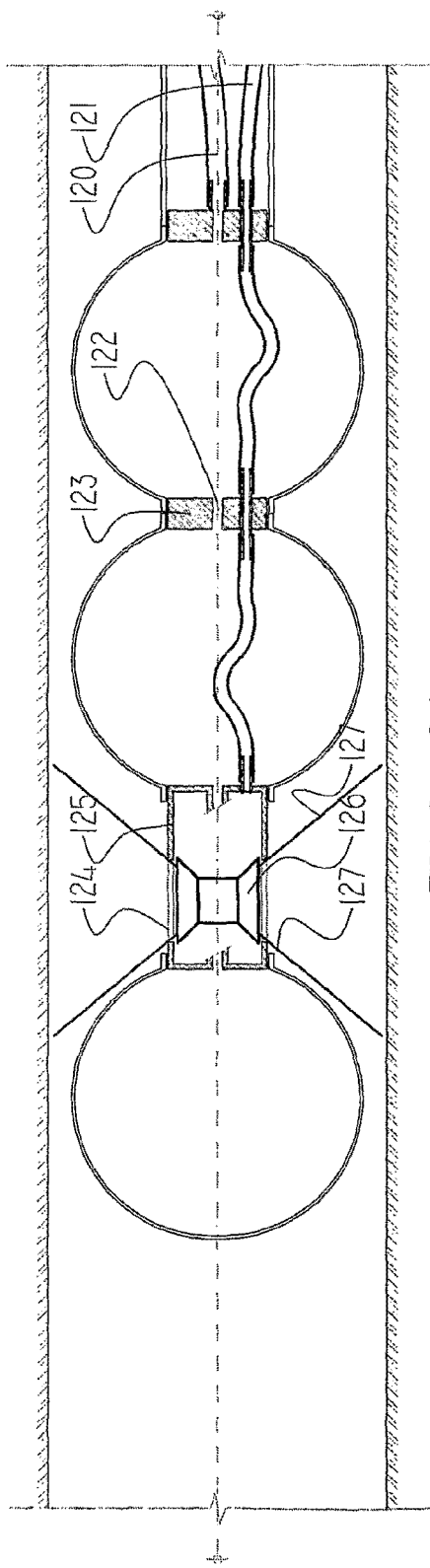
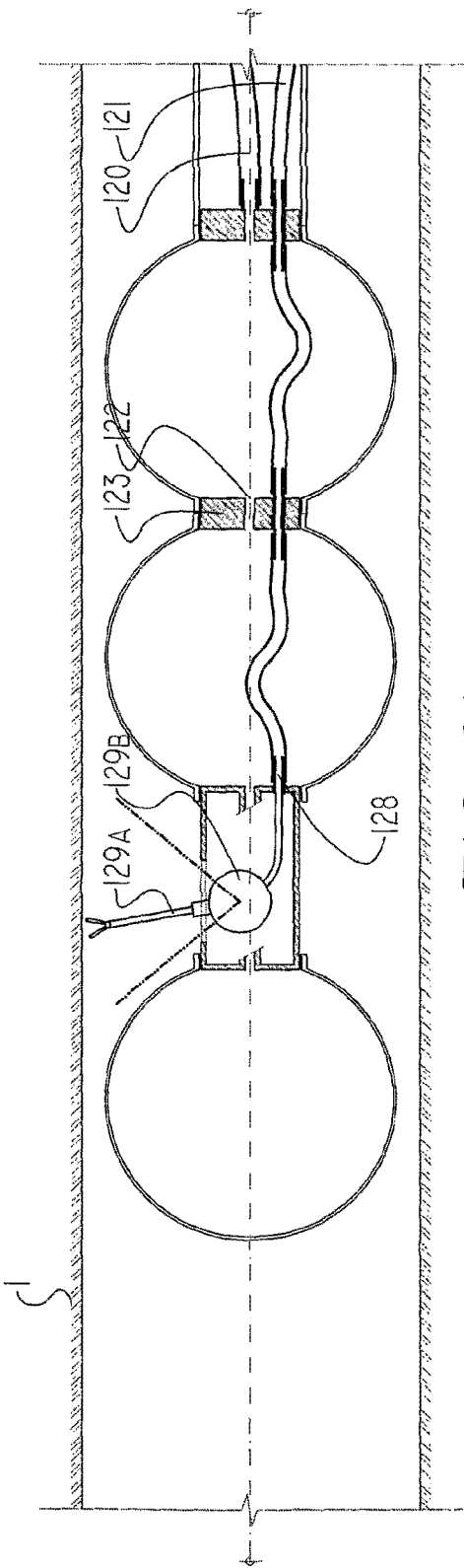
FIG 21A
FIG 21B

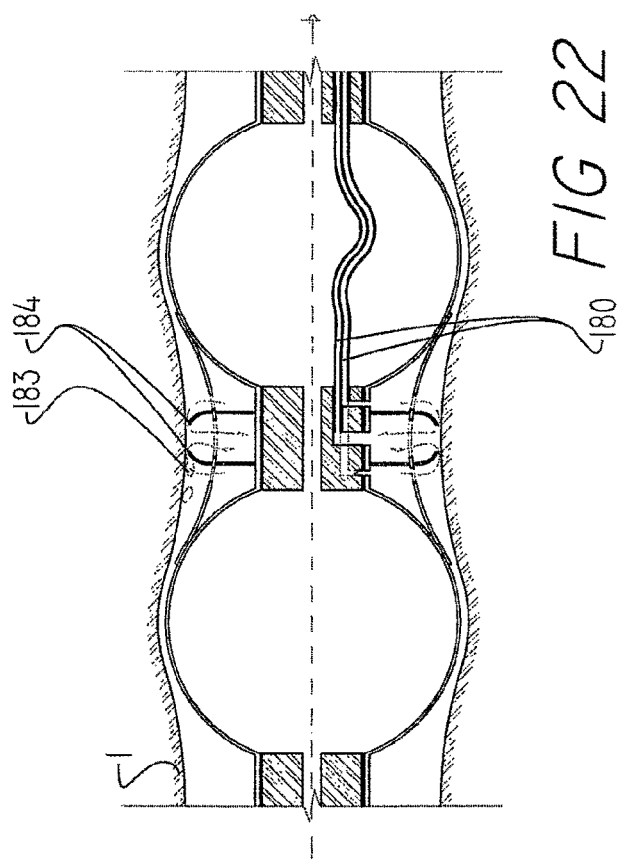

INFLATABLE BALLOON DEVICE AND APPLICATIONS

This is a 35 U.S.C. §371 application of PCT/IL2008/000180, filed Feb. 12, 2008, and claims the benefit under 35 U.S.C. §120 of said PCT application, and further claims the benefit under 35 U.S.C. §119(e) of U.S. Provisional Patent Application U.S. Ser. No. 60/900,698, filed Feb. 12, 2007. The contents of these priority applications are incorporated herein by reference.

FIELD OF THE INVENTION

The present invention relates to the field of inflatable devices capable of self propelled motion through tubes, especially for endoscopic and vascular use.

BACKGROUND OF THE INVENTION

The ability to crawl through long, flexible, and curved tubes has long been a challenge for engineers since numerous applications can benefit from a reliable solution. This ranges from medical applications for treatment and diagnosis to sewer pipes, gas pipes and power plants.

Current solutions often contain a payload such as a camera, that is pushed from the back by a long flexible rod or wire. This is the solution currently used in most medical applications with guide wires or catheters as used to deliver diagnosis or treatment instruments to the desired position, e.g. catheterization, colonoscopy, ureteroscopy, dilating balloon, and others.

In some type of applications it is impossible to push the active head from the back because the force required would cause buckling of the long rod or wire. One of the biggest shortcomings of current endoscopes and catheters is that they are pushed into the human body manually over a curved path, thereby causing friction, and possible injuries to the inner tissue walls of the lumen.

In search for a solution, a number of locomotion types of propulsion have been developed, which pull at the distal end of the lumen rather then pushing at the proximal end. Examples in non-medical applications include crawling vehicles and spider-like robots, such as are described in U.S. Pat. Nos. 6,824,510, and 5,090,259. In medical applications the most common solution is that of the inch worm type, that advances by means of peristaltic motion, such as is described, for instance, in U.S. Pat. Nos. 6,764,441, 4,176,662, 5,090, 259, 5,662,587, 6,007,482 and 5,364,353, and in the article by P. Dario, et al., "Development and in vitro testing of a miniature robotic system for computer-assisted colonoscopy," published in Computer Aided Surgery, Vol. 4, pp. 1-14, 1999, and in the article "A Locomotive Mechanism for a Robotic Colonoscope" by Byungkyu K, et al., published in Proceedings of the IEEE/RSJ Intl. Conference on Intelligent Robots and Systems; 2003, pp. 1373-8. Another type of medical application device is described in U.S. Pat. No. 6,702,735.

Another solution is one which imitates the locomotion of the earth-worm (Annelida), that generates waves of contraction and relaxation of alternate muscle groups (longitudinal and circular muscles), causing the worm to move forward, such as is described in the article by J. Dietrich et al., entitled "Development of a peristaltically actuated device for the minimal invasive surgery with a haptic sensor array" published in Micro- and Nanostructures of Biological Systems, Halle, Shaker-Verlag, 69-88. ISBN 3-8322-2655-9. Another solution suggested uses motion hydraulically generated close to the tip, such as is described in U.S. Patent Application 2005/0033343, for "Catheter Drive" to I. Chermoni.

Most of the above described devices have the disadvantage that a number of control lines or pneumatic tubes are required to operate the device, which complicates both the control system and the physical deployment of the device within the passageway. The device described in the above-mentioned U.S. Pat. No. 5,364,353 for "Apparatus for advancing an object through a body passage" to M. T. Corfitsen et al., and that in co-pending PCT Application No. PCT/IL2006/000925 for "Tip propelled device for motion through a passage" to the authors of the present application, on the other hand, require only one inflation tube. In U.S. Pat. No. 5,364,353, there is described a device using a single bladder and an axially expandable bellows with a throttle valve between them. A tube is provided with a lumen for the supply and removal of inflation medium to the bladder and bellows. The throttling valve ensures that the inflation of the bladder is delayed relative to the axial expansion of the bellows as pressure is applied to the inflation tube, and that the deflation of the bladder is delayed relative to an axial contraction of the bellows as pressure is released from the inflation tube, such that the device can be advanced stepwise through, for instance, a gastrointestinal canal.

In co-pending PCT Application No. PCT/IL2006/000925, there is described a device having a plurality of inflatable chambers arranged serially, and serially interconnected by means of small orifices, openings or tubes between adjacent chambers, in which at least the first and last chambers are expandable at least radially, and also optionally axially, and other intermediate chambers, if present, are expandable at least axially and also optionally radially. A tube is provided with a lumen for the supply and removal of inflation medium to the chambers. The small orifices, openings or tubes ensure that the inflation of one chamber relative to that preceding it is delayed, such that the chambers inflate sequentially as fluid is pumped into an inflation tube. Likewise, the deflation of a chamber is delayed relative to that in front of it as pressure is released from the inflation tube, such that the device can be advanced stepwise through, for instance, a gastrointestinal canal.

Many of the above described devices may have various disadvantages which limit their usefulness in one aspect or another, such that there is need for a new, distally propelled catheter head which can operate simply, over long tracts of internal passages, and without causing undue damage to the inner walls of the passages.

It is to be understood that the terms chamber, balloon, bladder and similar expressions used to describe the inflatable components of the various devices of the present application, may have been used interchangeably and even claimed thuswise, and it is to be understood that no difference is intended to be conveyed by use of one term or the other.

The disclosures of each of the publications mentioned in this section and in other sections of this application, are hereby incorporated by reference, each in its entirety.

SUMMARY OF THE INVENTION

The present invention seeks to provide new methods and devices for use in serial inflatable balloon self-propulsion devices, for motion along internal passageways, having features which are enabling for efficient use of such devices.

In a first aspect of this invention, embodiments are described whereby the device is maintained in a sufficiently rigid condition that it does not collapse when pushed into the lumen. Rigid balloon inserts or slidable or telescopic extensions to the segments between the balloons are able to accomplish this. Alternatively and preferably, a spring or an accordion-like trellis array can be attached between adjacent separators, such that a spatial relationship is maintained between adjacent balloons, while allowing some level of flexibility. Flexibility can also be imparted to the device by use of semi-flexible segment sections.

According to other embodiments of the present invention, there are described such devices in which the working channel is attached to the distal chamber of the device, such that it is pulled from the leading end of the device during inflation, rather than being pulled from the trailing end of the device during deflation. This provides more positive motion for a bigger payload, and better motion control. In such embodiments, a method is required to enable the fluid supply to be applied to the trailing sheath when the working channel moves relative to the trailing sheath in unison with the front balloon to which it is attached. This is done using a closed chamber with a section of curved working channel slack disposed therein.

Other aspects of the invention describe embodiments in which the trailing supply or service lines are carried in a coiled-up manner in a chamber carried at the rear of the device, such that it can be deployed rearwardly as the device progresses. Additionally, embodiments are described in which the supply of inflating fluid to either end of the serial array of balloons, enables the device to travel in either direction, depending on which end of the device the fluid is applied to.

A further aspect of the present invention relates to the provision of viewing or handling facilities to the device. By locating the viewing camera in between two distally positioned balloons, the device is able to provide observation capabilities to the lumen wall, yet without becoming excessively dirty by exposure to the front end of the device, as in prior art camera units. Additionally, a robotic biopsy arm or another treatment device can be easily mounted in the position between chambers, and to perform procedures on the lumen wall. Wall washing facilities are also available in that embodiment.

There is therefore provided in accordance with a preferred embodiment of the present invention, a self-propelled device for locomotion through a lumen, comprising:
(i) a set of serially arranged inflatable chambers, with a distal chamber at one end of the device, and a proximal chamber at the opposite end of the device,
(ii) a fluid supply system for inflating the chambers sequentially, such that during inflation, the device moves with the distal chamber leading, and
(iii) an axial channel running axially through the device, the channel being attached to a distal part of the device.

In such a device, it is the motion of the device through the lumen that pulls the axial channel with it. The axial channel may preferably be attached to either one of the distal chamber or the chamber immediately proximal to the distal chamber.

Furthermore, in accordance with yet another preferred embodiment of the present invention, in any of the above-described devices having a channel attached to a distal part of the device, the fluid for inflating the chambers may preferably be supplied through a sheath enclosing the axial channel. Alternatively and preferably, the fluid for inflating the chambers may be supplied through a separate supply tube.

In accordance with yet another preferred embodiment of the present invention, in such a device having a sheath around the axial channel, the fluid supply system may preferably comprise a hermetically sealed rigid chamber, the chamber comprising:

(i) an input port for inputting fluid to the rigid chamber,
(ii) an output port for outputting fluid to the sheath for inflating the inflatable chambers, and
(iii) a working channel port to which the proximal end of the axial channel is attached after traversing the rigid chamber in a path having a length of slack channel.

In such a case, motion of the distal chamber of the device is operative to pull the axial channel, such that the length of slack channel shortens.

In the above described devices with an axial channel attached to a distal part of the device, the inflatable chambers may preferably have the form of an annulus, the axial channel running through the annulus and outside of the inflatable volume of chambers, and wherein the fluid for inflating the chambers is supplied by a tube separate from the axial channel. Alternatively and preferably, the axial channel may be adapted to accommodate functional leads to either one of a viewing system and an operating tool system carried at the distal end of the device.

There is also provided in accordance with yet a further preferred embodiment of the present invention, a self-propelled device for locomotion through a lumen, comprising:
(i) a set of serially arranged inflatable chambers having separator segments between adjacent chambers,
(ii) a fluid supply system for inflating the chambers sequentially, and
(iii) a stiffening element inserted in at least one of the chambers, the stiffening element essentially filling the length of the at least one chamber when uninflated, such that when the at least one chamber is uninflated, the stiffening element provides the device with axial rigidity between the separator elements associated with the at least one chamber.

The above described device may also preferably comprise an axial member disposed axially along the device, wherein the stiffening element slides along the axial member as the at least one chamber inflates. The stiffening element may preferably have a tubular form, and may preferably be attached to a separator element.

In accordance with still another preferred embodiment of the present invention, the stiffening element may preferably comprise two overlapping elements, each attached to a separator element at opposite ends of a chamber, one of the overlapping elements sliding within the other as the chamber inflates.

There is further provided in accordance with still another preferred embodiment of the present invention, a device as described above, and in which the stiffening element may preferably comprise a spring attached to the separator elements at opposite ends of the at least one chamber, the spring having a closed length which essentially fills the length of the at least one chamber when uninflated. Alternatively and preferably, the stiffening element may preferably comprise an expandable cylindrical trellis structure attached to the separator elements at opposite ends of the at least one chamber, the trellis structure having a closed length which essentially fills the length of the at least one chamber when uninflated.

According to another aspect of the invention, in the above described device, the at least one chamber may preferably have an annular form, the device further comprising a central axial member running through the center of the annular chamber.

There is further provided in accordance with still another preferred embodiment of the present invention, a self-propelled device for locomotion through a lumen, comprising:
(i) a set of serially arranged inflatable chambers having separator segments between adjacent chambers, and (ii) a fluid supply system for inflating the chambers sequentially, wherein at least one of the separator segments is flexible, such that that part of the device in the vicinity of the at least one separator segment can negotiate a bend in the lumen by flexing of the at least one separator segment. In such a device, the at least one flexible separator segment may preferably have an interior that is inflatable, such that the flexibility of the segment can be controlled in accordance with the inflation pressure of the segment.

In accordance with a further preferred embodiment of the present invention, there is also provided a self-propelled device for locomotion through a lumen, comprising: (i) a set of serially arranged inflatable chambers, (ii) a fluid supply line for inflating the chambers sequentially, and (iii) a container carried by the proximal one of the inflatable chambers, the container comprising a compacted portion of the fluid supply line, such that as the device traverses the lumen, the fluid supply line deploys from the container. In such a device, the compacted portion of the fluid supply line may preferably be a coiled portion.

There is even further provided in accordance with another preferred embodiment of the present invention, a self-propelled device for locomotion through a lumen, comprising:
(i) a set of serially arranged inflatable chambers, having at least a distal and a proximal chamber, and
(ii) a fluid supply system for inflating the chambers sequentially, wherein the fluid supply system may preferably be connectable to the proximal chamber and to the distal chamber, such that the device can move in either direction in accordance with which of the chambers is supplied with fluid. In such a device, the fluid supply system may preferably be connectable to the proximal and distal chambers either by separate supply lines, or by a single supply line directed to one or the other of the proximal and distal chambers by means of a valve.

Furthermore, in accordance with yet another preferred embodiment of the present invention, there is also provided a self-propelled device for locomotion through a lumen, comprising:
(i) two sets of serially arranged inflatable chambers, each having least a distal and a proximal chamber, the sets being connected serially, and
(ii) a fluid supply system for inflating the chambers of each of the sets sequentially, wherein the fluid supply system is connectable to a proximal chamber of one set and to a distal chamber of the other set, such that the device can move in either direction in accordance with which of the chambers is supplied with fluid. In such a device, the fluid supply system may preferably be connectable to the proximal and distal chambers either by separate supply lines, or by a single supply line directed to one or the other of the proximal and distal chambers by means of a valve.

There is also provided in accordance with a further preferred embodiment of the present invention, a self-propelled device for locomotion through a lumen, comprising:
(i) a set of serially arranged inflatable chambers,
(ii) a fluid supply system for inflating the chambers sequentially, and
(iii) a flexible tubular membrane enclosing at least one pair of adjacent chambers, the membrane having at least one orifice disposed in the region between the at least one pair of chambers.
This device is preferably such that when the at least one pair of chambers are inflated, the pressure within the flexible membrane falls and any collapsible part of the lumen is pulled onto the membrane, sealing the orifice.

In accordance with yet another preferred embodiment of the present invention, there is also provided a self-propelled device for locomotion through a lumen, comprising:
(i) a set of serially arranged inflatable chambers,
(ii) a fluid supply system for inflating the chambers sequentially, and
(iii) an operating pod disposed between the distal one of the chambers and the chamber immediately proximal thereto.
The operating pod may preferably contain either or both of a viewing device directed at the lumen wall, and a surgical tool disposed such that it can perform a surgical procedure on the lumen wall.

Finally, in accordance with still another preferred embodiment of the present invention, there is provided a self-propelled device for locomotion through a lumen, comprising:
(i) a set of serially arranged inflatable chambers,
(ii) a fluid supply system for inflating the chambers sequentially, and
(iii) an operating pod disposed either between a pair of the chambers or at the distal tip of the device, the pod comprising a system for cleaning the inside surface of the lumen as the device proceeds therethrough.
In such a device, the cleaning system may preferably be supplied with cleaning fluid by a supply line running through the device. Additionally, the cleaning system may further comprise a flushing line for removing debris cleaned from the lumen wall by the cleaning system.

BRIEF DESCRIPTION OF THE DRAWINGS

The present invention will be understood and appreciated more fully from the following detailed description, taken in conjunction with the drawings in which:

FIGS. 3A to 3C illustrate embodiments of the present invention to overcome potential difficulty in inserting an inflatable balloon device into a lumen to be negotiated, and in enabling it the device to progress freely once inserted;

FIGS. 4A and 4B illustrate more preferred embodiments for providing axial stiffness to an inflatable balloon device;

FIGS. 5A-5C illustrate another preferred embodiment in which axial stability is guaranteed by a flexible spring inserts operating in accordion fashion;

FIGS. 6A-6B illustrate another preferred embodiment similar to that of FIGS. 5A-5C, but using an extendible trellis structure;

FIGS. 7A and 7B illustrate more preferred embodiments for providing axial stiffness to an inflatable balloon device, using separator elements with extended inter-sliding end extensions;

FIGS. 8A-8B illustrate another preferred embodiment for providing axial stiffness to an inflatable balloon device, using floating rings within the balloons;

FIGS. 9A-9G illustrate another preferred embodiment of an inflatable balloon device, in which the working channel is attached to the tip of the device to provide improved traction;

FIGS. 10A-10G illustrate another preferred embodiment similar to that of FIGS. 9A-9G, but using annular balloons;

FIGS. 12A-12C illustrate embodiments which allow the inflatable balloon device to bend by providing flexible separator sections between balloons;

FIGS. 13A and 13B illustrate another preferred embodiment of the present invention, in which the supply line and/or working channel are deployed rearwards during propulsion;

FIGS. 14A and 14B illustrate another preferred embodiment of the present invention, which enables the device to travel backwards out of the lumen, as well as forwards into the lumen;

FIG. 15 and FIGS. 16A and 16B illustrate alternative embodiments of devices which can be propelled in both directions.

FIGS. 17A-17D, FIGS. 18A-18D and FIGS. 19A-19D illustrate alternative methods of manufacturing balloons for use in the devices of the present invention;

FIGS. 21A and 21B illustrate another preferred embodiment of the present invention, which enables the device to view the lumen inner wall using a camera built into an inter-balloon compartment, to clean the wall being viewed, and to perform surgical procedures on the wall; and FIG. 22 illustrates another preferred embodiment of the present invention for providing a wall cleaning ability to the instrument.

DETAILED DESCRIPTION OF PREFERRED EMBODIMENTS

Figure 1:
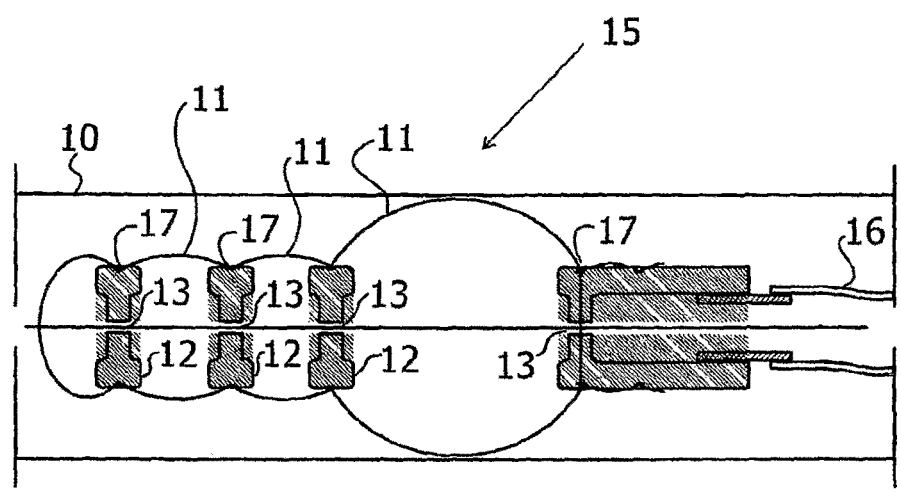
FIG. 1 illustrates schematically a tip-propelled catheter device, constructed and operative according to a first preferred embodiment of the present invention.

Reference is now made to FIG. 1, which illustrates schematically a tip-propelled catheter device 15 for traveling down a lumen 1, as is known in the art. The device may preferably comprise a number of balloons 11 connected to each other by separators 12 with one or more small openings, preferably in the form of orifices 13 formed therein, such that all the balloons comprise a single volume, inflatable through a single input. For ease of construction, the device can alternatively and preferably comprise a single inflatable balloon divided into separate balloon segments by separators with orifices such that the entire segmented balloon can be inflated through a single input. The balloon fabric is preferably held in place relative to the separators 12 by means of rings 17 or glued or molded to the separators. Whichever preferred construction is used, the device is connected by a single tube 16 to a fluid supply for inflating the balloons or the balloon segments. For the sake of simplicity, the operation of the device will be explained using the term balloon for each separate segment, although it is to be understood that the invention can equally be implemented using a single balloon segmented to form the separate segments. The inflation fluid used can be any one of a compatible gas or liquid. The fluid supply can alternatively be taken from the passageway through which the device is moving, by means of an on-board pump, and ejected thereto after use.

Figure 2A:
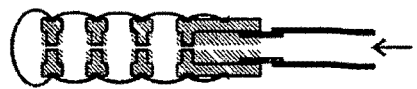
FIGS. 2A to 2I illustrates schematically how the fluid inflates the balloon cells of the device of FIG. 1 in a sequence that causes the device to move forward.
Figure 2B:
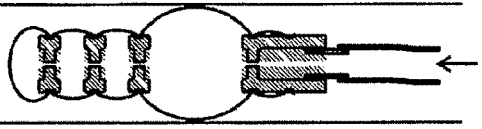
Figure 2C:
Figure 2D:
Figure 2E:
Figure 2F:
Figure 2G:
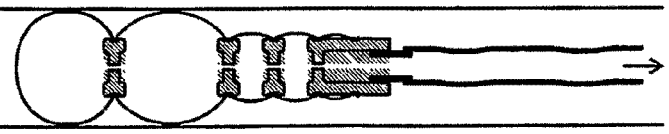
Figure 2H:
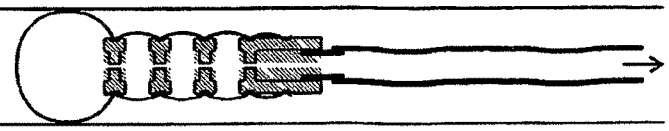
Figure 2I:
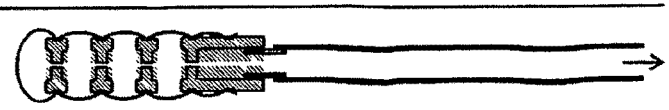

Reference is now made to FIGS. 2A to 2I which illustrates schematically how the fluid inflates the balloon cells in a sequence that causes the proximal one to inflate first, increasing its diameter as well as its length. Being inflated, it locks itself against the inside walls of the tube, but at the same time, its increase in length advances the other cells which are not fully inflated yet and hence are not locked on the inside walls of the tubes. The cells are inflated in a sequence until the distal cell locks against the inner tube walls, but at a position further along the tube than that of the un-inflated balloon distal cell initial position. This situation is reached in FIG. 2E. The timing and order of the sequence is mandated by the fluid flow dynamics through the orifices, and the dynamics of the balloon inflation. Disconnecting the supply and allowing the fluid pressure to drop at this point, or pumping out the fluid, as shown in FIG. 2F, causes the proximal cell to deflate first reducing both its length and diameter. Since the distal cell and all of the intermediary cells, are at this point still fully inflated, they are still locked against the inner walls of the tube, thus pulling the proximal cell inward as the balloon deflates and decreases its length.

The sequential motion series is repeated inducing motion of the entire device as can be seen in FIGS. 2A to 2I. The locomotion sequence is composed of two phases: inflation and deflation, with the arrows at the entrance of the inflation tube indicating the direction of fluid flow. A simplified description of the dynamics of the sequential inflation is as follows:

The flow through an orifice is proportional to the square root of pressure difference across the orifice, and the square of the diameter of the orifice, such that the orifice sizes can be selected to provide specific inflation dynamics.

Inflation phase: Initially, the pressure is equal in each balloon and is equal to the outside pressure, therefore the balloons are in deflated condition, as in FIG. 2A. When the pressure in the supply tube rises, the fluid begins to flow through the first orifice into the first (proximal) balloon, as in FIG. 2B. The pressure difference between the first and second balloons is now lower than the pressure difference between the supply tube and the first balloon, such that the flow rate in the second orifice is slower and the second balloon inflates more slowly than the first one. By this means, the pressure propagates in a gradual manner to the last (distal) balloon until the pressure in all the balloons is equal, as shown in FIG. 2E.

Deflation phase: Now the pressure in the supply tube is reduced to the outside pressure, or the fluid is pumped out of the inflation tube, and there is then a pressure drop between the supply line and the first balloon. The fluid begins to flow out of the first balloon, as in FIG. 2F. Again, since the pressure difference between the supply tube and the first balloon is greater than between the rest of the balloons, the first balloon deflates first, then deflates the second, and so on until the last balloon is deflated, as in FIG. 2I.

In a variation of the actuation sequence, it is possible to initiate the cycling process even before the last cell is fully deflated. In such a case there will always be a base point anchored to the passageway and hence will prevent unwanted slippage in the case of external forces. Different orifices sizes, or different numbers of orifices, can be used between different positioned balloons to improve the locomotion and speed of the device, all according to the dynamics of the fluid flow in to, out of, and between balloons. Furthermore, the viscosity of the inflation fluid can be chosen to improve the locomotion dynamics.

In some applications of the devices shown in FIG. 1 and FIGS. 2A-2I and in many of the other embodiments described in co-pending International Application No. PCT/E12006/000925, and such as are described in other documents describing serial inflatable balloon devices, there may be difficulty in inserting the device into the lumen to be negotiated, and there may also be difficulty in enabling it to progress freely once inserted.

The insertion problem may arise if the device has a structure which is so flexible that there may be some difficulty inserting it into the body or the pipe by pushing. It may then be desirable to increase the axial stiffness, to facilitate entry by pushing, but preferably without altering the propulsion capabilities.

The propagation problem may arise if the proximal inflating balloons tend to compress the array of distal balloons, rather than pushing them and their payload forward. This problem may be exacerbated in the presence of the first problem of lack of axial stiffness.

Reference is now made to FIGS. 3A to 3C, which illustrate preferred embodiments of the present invention, in order to solve these two potential problems. In FIG. 3A, there is shown a device of the type described in FIG. 1 and FIGS. 2A-2I herein, and in co-pending International Application No. PCT/E12006/000925, passing though a lumen 1, and having balloons 4A, 4B etc, separators 10A, 10B, etc, and passages 3, for allowing flow of the inflating fluid between balloons. It is observed that although the separators 10A, 10B, etc., may be stiff, the intrinsic flexibility of the balloons 4A, 4B, etc., may cause the device to be too "floppy" to be easily inserted or easily propelled. Furthermore, in FIG. 3B, there is also shown how, by inflation of a proximal balloon 4A, the more distal balloons 4B, etc., tend to be compressed rather being pushed forward.

Reference is now made to FIG. 3C, which illustrates a first preferred embodiment to alleviate these problems and to provide more uniform propagation of the device. In FIG. 3C, stiffening elements 9 are inserted into the device between the separator sections. The length of the stiffening elements 9 is selected so that when the device is uninflated, there is a row of solid segments along the length of the device, thus increasing stiffness and facilitating entry. As the device is inflated sequentially, this continuous row of solid segments is operative to mechanically push the entire distal parts of the device forward as the proximal balloons inflate.

Although the device shown in FIGS. 3A to 3C is of the type which includes a central channel or a guidewire passing through the balloons, it is to be understood that this embodiment is equally applicable to a device without such a central channel or guidewire, on condition that some means of positional support is provided for the stiffening elements 9, to keep them aligned with each other.

Reference is now made to FIG. 4A, which illustrates another preferred embodiment, in which the stiff core of the separator/orifice element 20A is axially extended such that in the deflated position, the distal end of the element 20A touches the proximal end of the separator/orifice element 20B of the neighboring section. This solution improves the ability of the device to be pushed over the guidewire without folding up the balloons. The guidewire at the center of the orifices gives axial stability. FIG. 4B shows the device extending as the balloons are inflated. Special openings 23 allow non-stop flow even if the gap 3 between the sequential orifices sections is closed. Additionally and alternatively, if the shape of the protrusion 25 is constructed such that its contact surface with the following orifice section is not flat, but has fluid release passages cut into its profile, such a construction will allow flow even when the protrusion 25 touches the following orifice section.

Figure 5C:
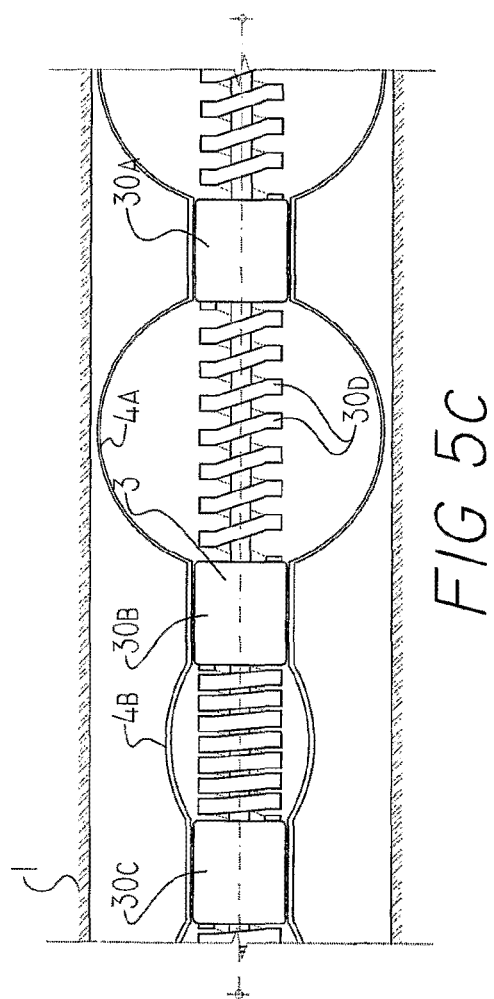
Figure 9E:
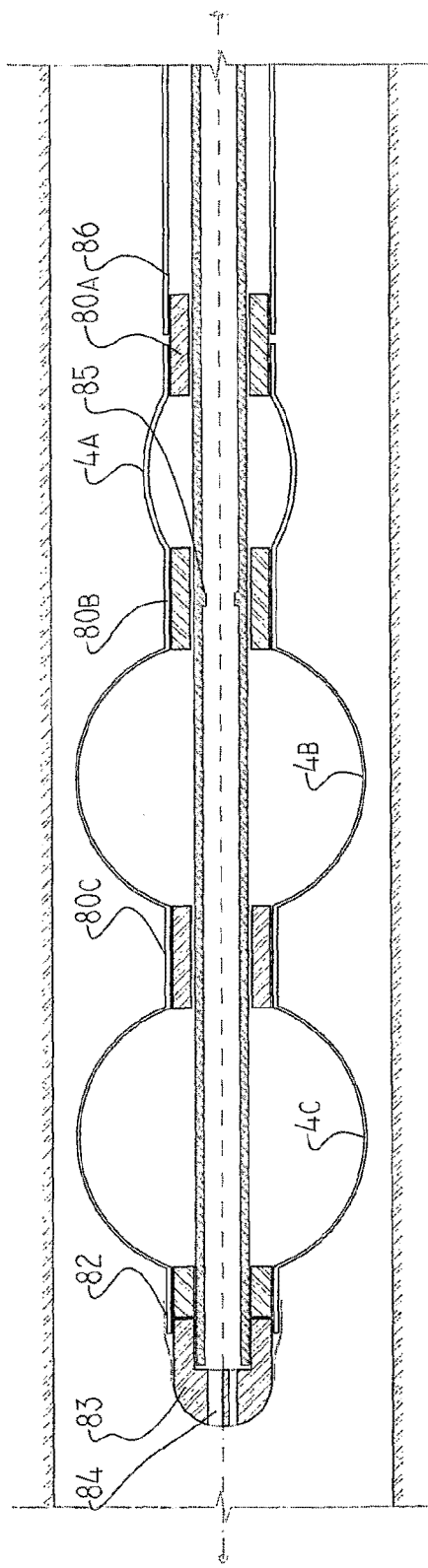
Figure 9F:
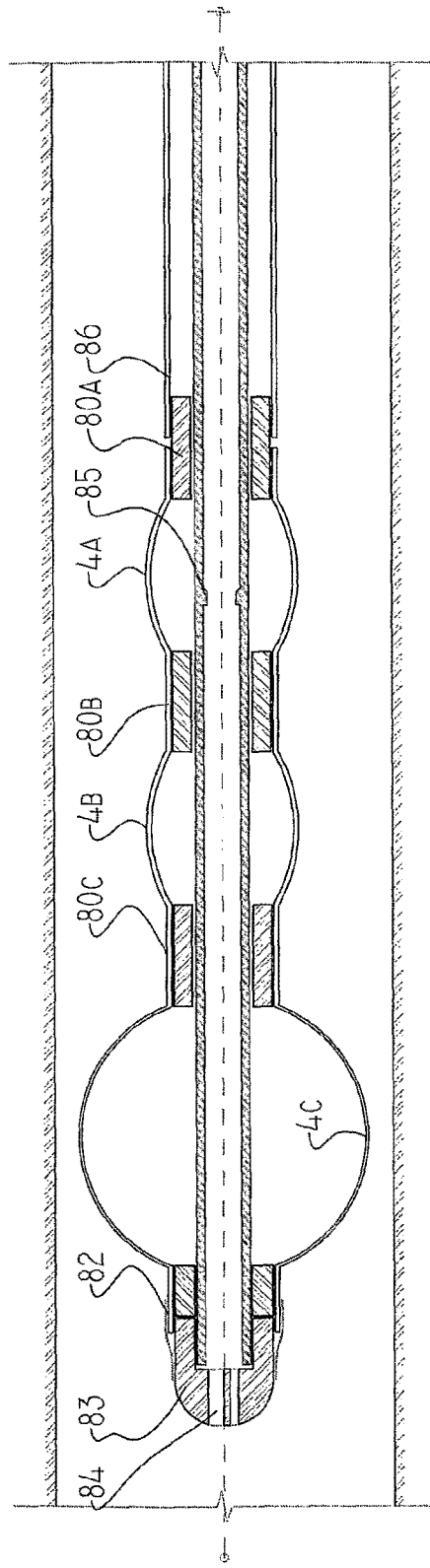
Figure 9G:
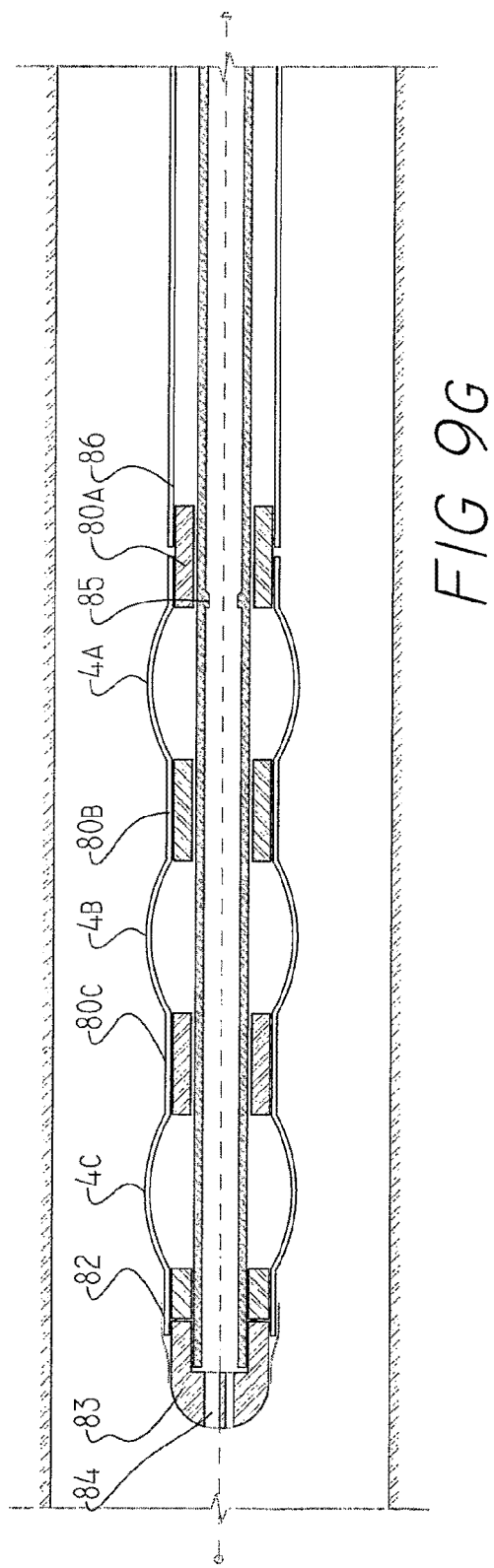
Figure 10G:
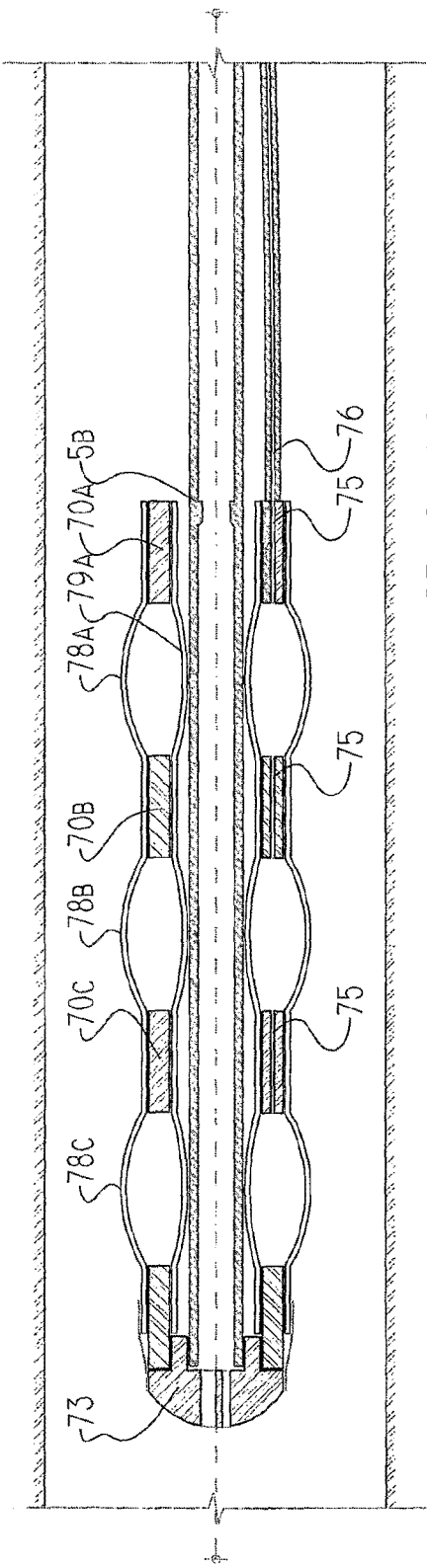

Reference is now made to FIGS. 5A to 5C, which illustrate another preferred embodiment in which the axial stability is guaranteed by a flexible spring 30D between the separator/orifice elements 30A, 30B, 30C, operating in an accordion fashion. The spring has a limited solid length in its closed position, and is extendible in the axial direction with the stretching of the inflated balloons. The closed stance of the spring is shown in FIG. 5A. The open stance is shown in two different views in FIG. 5B, which is a cross section of the device with spring, and in FIG. 5C, which is a side view. The well-defined closed length of the spring allows for axial stiffness and push-ability of the device, while not limiting axial extension of the balloons for propulsion.

Reference is now made to FIGS. 6A to 6B, which illustrate another preferred embodiment similar to that of FIG. 5A but with the spring replaced by axially extendable trellis-like extendible elements, 40A, 40B, 40C, 40D, which do not allow relative rotation between separator/orifice elements 41A, 41B, 41C, which the spring embodiments of FIGS. 5A to 5C do. The axially extendable elements may be designed with a double trellis structure, as shown in elements 40A, 40B of FIG. 6A or with a single extendible structure, as shown in elements 40C, 40D of FIG. 6B, or with any other similar design allowing axial extension, limited compression and axial rotational stability.

Reference is now made to FIG. 7A, which illustrates another preferred embodiment for achieving the effect shown in FIGS. 4A and 4B. In FIG. 7A, the separator/orifice elements 50A, 50B, etc., are constructed with extended inter-sliding end extensions, so as to create telescopic motion between the separator/orifice elements which give extended axial stability even without the need for a guidewire. The special openings 51B, in the extensions allow unimpeded flow of fluid between the telescopic sections, since they allow free flow of the fluid from the gap section 51C around the guidewire, from where the fluid is supplied, out into the balloon volume 51A for inflating the balloons 4. The openings 51B must be of such a size and spaced apart by such a distance that regardless of the mutual position of the two sliding extensions, there will always be at least one set of openings aligned such that the fluid can pass from the gap section 51C to the balloon volume 51A.

Though the embodiments of FIGS. 7A-7B show a guidewire running axially through the center of the device, it is to be understood that this arrangement could equally be applicable for an embodiment with a channel running through the device. It is to be understood that this comment, and its reverse, is applicable for all of the embodiments shown in the application having axially running elements. Such elements can generally be guide wires or channels, except of course in those embodiments where one or the other is mandated by the intended use.

Reference is now made to FIGS. 8A to 8B, which illustrate another preferred embodiment of the present invention, in which rings 62 of similar cross sectional shape and size to that of the separator/orifice elements 60A, 60B, 60C are inserted into the balloons. Orifices 63 within the body of the separator elements provide flow of inflation fluid between balloons. In the example shown in the embodiment of FIGS. 8A to 8B, the balloons are of the annular type around the walls 5 of an internal channel 6. The rings 62 are free to move axially inside the balloons. They provide axial stiffness when pushing the device, both during insertion or during propagation.

One of the main uses of the tip-propelled devices described in this application is to propel an endoscope and/or therapeutic tools into a bodily passageway. The endoscopic vision system is usually fixed to the tip of the device, while the optical/electrical connections and tool insertion generally require a special "working channel", which goes all the way through the device from the rear to the tip. The goal of the device is to propel the working channel into the passageway, with the payload and operating point at its front end. In the embodiments described so far, the device has generally been simply regarded as a locomotion device for pulling its trailing channel into the passageway, and any working channel has been considered as being simply attached to the rear end of the device and pulled through. This pulling action in the prior art devices, occurs when the set of balloons deflates, with the distal balloon anchored at the furthermost point of the passageway, and the deflation pulling up the rear of the device with the working channel attached thereto.

According to further preferred embodiments of the present invention, the working channel is connected to the distal end (tip) of the device and not to the tail of the device. This arrangement endows the device with propulsion dynamics having significant advantages over previously described tail attached embodiments, in that a stronger pulling force is obtained on the working channel. This pulling force does not depend on the flexibility of the balloons during deflation, as in the previously described embodiments, but rather, arises from a pulling action, generated by positive pressure in the balloons during the inflation cycle. This is known as an inverted cycle device.

Reference is now made to FIGS. 9A to 9G, which illustrate the action of a preferred embodiment of the present invention, using the improved traction arrangement described above, in which the working channel is attached to the tip of the device. In the embodiment shown in FIG. 9A, the working channel 81 is connected to the tip 83 of the device, and the end may preferably be secured with a cover 82. The gap between the working channel 81 and the trailing outer pipe or sheath 86 may preferably serve as a supply line of fluid for inflating the balloons. The gap between separator section 80 and working channel 81 may preferably serve as the orifice for transfer of inflation fluid from balloon to balloon and for delay of the inflation/deflation process. The same gap also allows for free sliding of separator sections 80A, 80B, 80C over the working channel 81. At the very tip of the device 84, endoscopic surveillance can be conducted and/or therapeutic tools can be applied to the inside of the passageway.

During the inflation phase, the balloons are sequentially inflated, as described in FIG. 1 and FIGS. 2A-2I of this application, or as in co-pending International Patent Application No. PCT/I12006/000925, or as in other sequential balloon embodiments described in other patents and articles, and push the tip of the device forward. The tip thus pulls the working channel which is connected to it. During the deflation phase, the outer pipe or sheath 86 is pulled forward by the deflation of the balloons 4A, 4B, 4C, etc., employing the natural elasticity of the material of the balloons, while the working channel is anchored at its forward-most position.

A marker sign 85 is shown on the working channel in the drawings, to illustrate the propagation of the working channel forward with progress of the device through FIGS. 9B-9G. It should be noted that the mark has been added only in the drawings to illustrate the progress of the motion, but that it is not meant to be a part of the device itself.

The advantage of propulsion using this arrangement is that the potentially heavy, bulky working channel is pulled during the more powerful inflation phase, where the internal supplied, positive inflation pressure is used, rather than during the deflation phase where only the elastic properties of the balloon material relaxing provide the propulsion force.

Reference is now made to FIGS. 10A to 10G, which illustrate the action of another preferred embodiment of the present invention, similar to FIGS. 9A to 9G in that the working channel is connected directly to the tip 73 of the device. At the very tip of the device 74, endoscopic surveillance can be conducted and/or therapeutic tools can be applied to the inside of the passageway.

In the preferred embodiment of FIGS. 10A to 10G, the balloons 78A, 78B, 78C, are annular in shape, such that an additional balloon wall 79A separates the balloon volume 78A from the working channel 71. The flow delaying orifices 75 are now located inside the separator sections 70A, 70B, 70C. The working channel is thus totally separated from the device inflation fluid, which is preferably supplied by means of a separate low profile supply pipe 76. The supply pipe 76 can therefore be made thin and flexible making the device tail lighter in weight than in the embodiment of FIGS. 9A to 9G where an outer sheath is used to supply the inflation fluid.

The advantage of the annular, double balloon system and the concomitant separation of the inflating fluid from the working channel allows for smoother operation, more precise orifice cross section, and extended bending capabilities of the device. The friction between the working channel 71 and the inner balloon wall 79A should be small. A lubricant material can be used to lower the friction and to allow for free sliding between them. The supply line 76 and working channel 71 may preferably be enclosed by an outer sheath (not shown), which can be lightweight. As in FIGS. 9A to 9G, a marker 5B is shown on the working channel to indicate the movement of the working channel at each successive balloon inflation.

In the preferred embodiments of FIGS. 9A to 9G, the working channel 81 moves axially inside the separator/orifice sections 80A, 80B, 80C. The working channel 81 is connected to the tip and is therefore pulled forward. This means that the length of working channel should be independent of the length of the supply line 86, since the working channel has a longer range of motion than the supply line.

Figure 11A:
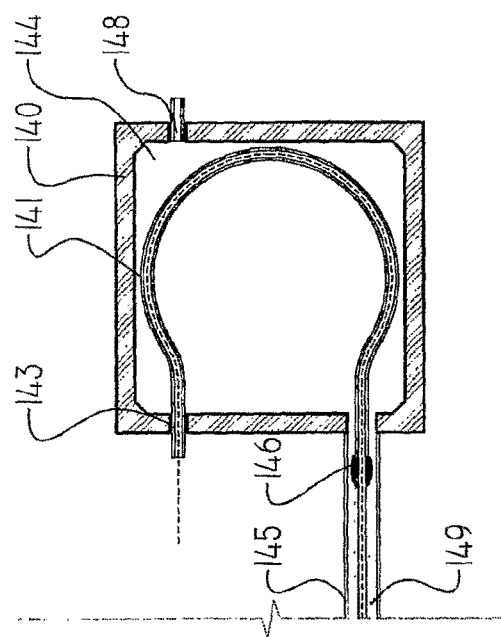
FIGS. 11A and 11B illustrate a termination chamber compensating for the different changes in length of the working channel and the supply line in the embodiments of FIGS. 9A-9G and 10A-10G as the device progresses.
Figure 11B:
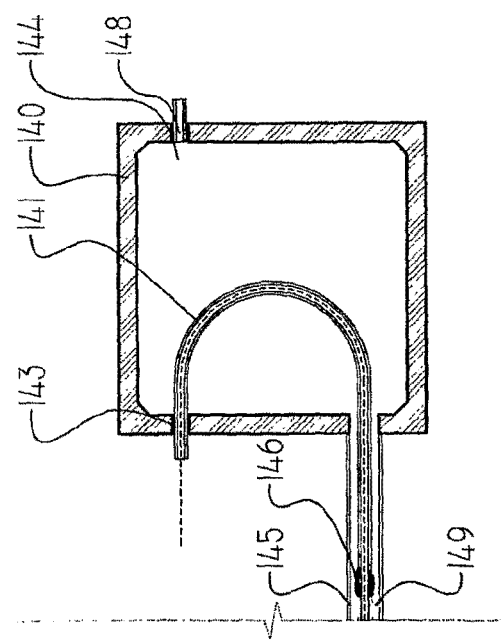

Reference is now made to FIGS. 11A and 11B which illustrate preferred embodiments of a length compensation mechanism for achieving this length separation, by means of a hermetically closed termination chamber 140. In FIG. 11A, there is shown the entry point 143 of the working channel at its normal length. The working channel is coiled up 141 in an arc. When the balloons are inflated, the working channel 141 is pulled forward to the position shown in FIG. 11B. The marker sign 146 shows the movement of a length of the working channel, which is the difference between the length of the inflated and deflated balloons of the device. The fluid for inflation of the balloons resides within the termination box 140 in the area 144 and flows freely between the working channel and the outer supply line 149. The input connector 148 for the inflating fluid can be placed anywhere in the box 140, such that it will apply pressure to the volume of fluid 144. The dimension 147 marks the motion of the working channel for a single balloon inflation step.

Since pressure in a cylindrical balloon stretches the balloon skin and puts it under tension, inflated balloons connected by rigid separator sections, as in the previously shown embodiments, resist any tendency of the device to bend, such as is required when negotiating curves in the lumen. In order to overcome this problem, a number of further preferred embodiments are shown in FIGS. 12A to 12C, which allow the device to bend by providing flexible separator sections between balloons 100A and 100B. In the preferred embodiment of FIG. 12A, the separator/orifice section is separated into two parts 102, with a flexible pipe 103 between the two sections to allow for the fluid flow. The whole separator/orifice section can be made of very flexible material, while ensuring that its flexibility is such that the fluid passage through the orifice is not blocked by the bending. A flexible sheath 108 preferably keeps the gap between the balloons clear and provides free angular motion between the balloons.

FIGS. 12B and 12C show a further embodiment of a flexible joint device, with the ability for variable joint stiffness. A joint pressurizing pipe 104,105 is added to the device, running from the internal volume of one separator section to the next, without interfering with the fluid pressures needed for device propagation. If a pressurized fluid is supplied into the pipe 104, 105, pressure is increased within the internal volume of the separator section. This separator section has a flexible outer covering 101, and when it is pressurized it straightens up and becomes stiffer. In such a way the stiffness of the joints can be controlled from very flexible to very stiff, in accordance with the internal pressure 106 supplied by the joint pressurizing pipe 104, 105.

Reference is now made to FIGS. 13A and 13B which illustrate another preferred embodiment of the present invention, in which the supply line 131 and/or working channel 133 are coiled up inside a storage unit 132 mounted on the rear of the device, and are deployed during propulsion. The orifice 130 supplies the inflation fluid to the first balloon. FIG. 13B shows the device after having moved forward, with part of the content of the storage unit 132 having been deployed. During such operation the device does not need to pull the supply line and/or working channel, thus eliminating friction of the channel with the walls of the passage being traversed.

Reference is now made to FIGS. 14A and 14B which illustrate another preferred embodiment of the present invention, which enables the device to travel backwards out of the lumen, using a similar positive propulsion mechanism to that described hereinabove for the forward propulsion. In the embodiment of FIG. 14A, an additional fluid supply line 113 preferably passes through the length of the device, and is connected to the distal balloon 112D at the tip. The fluid supply preferably passes from segment to segment by means of an additional orifice in the separator/orifice sections 111, with the separate supply line 113 connecting the orifices. This embodiment requires two trailing fluid supply lines, one 115 connected by orifice 114 to the proximal balloon 112A for forward motion and one 116, connected to the distal balloon 112D through line 113 for the backward motion.

In the preferred embodiment of FIG. 14B, the device is supplied with only one global fluid supply line 118, and a valve 117 switches this supply either to the proximal balloon for forward motion or to the distal balloon for backward motion. When the inflation starts from the distal balloon, the sequence of inflation/deflation is reversed and backward propulsion is attained in a manner similar to forward prolusion.

There is an additional advantage of having control over the distal balloon inflation before that of the other balloons. When the device has reached its functional position, and it is desired to perform its intended procedure, it may be in a situation with all of the balloons deflated, such that the device is not anchored within the lumen. In order to effect such anchoring, using this embodiment, pressure can be supplied initially to the distal balloon, which may be the closest to the working point, in order to keep it inflated and anchored to the lumen.

According to a further preferred embodiment of the present invention, two or more devices may be connected, pointing in opposite directions as shown in FIGS. 15 and 16A, each complete with its own supply line. This provides the ability to use two single direction devices in one operative unit, which will have the ability to move in opposite directions, depending on which supply line is used.

In FIG. 15, one supply line 194 feeds the balloons 192A-192C at the distal end of the device, while line 195 feeds the balloons 191A-191C at the proximal end of the device. Orifices 193 set in the separating elements 190B-190F provide inter balloon connection in each set of balloons. A sheath 196 preferably covers the trailing supply lines.

In FIG. 16A, the supply lines 205, 206 are attached to the two sets of balloons 202A-C and 203A-C at their junction. The inflation fluid is passed from balloon to balloon through orifices 201 in the separators 200.

According to another embodiment of similar nature, both oppositely facing devices may have a common supply channel but activated by different pressures, for example, by means of a pressure sensitive valve 207 as shown in FIG. 16B, or, by selecting the size or thickness of the balloons of the two devices such that they will operate at different pressures, or simply by means of a 2-way valve 207.

According to a further preferred embodiment of the present invention, the device is propelled to the end of the colon preferably while screening, recording and taking images, as is usual in colonoscopy. In case a further treatment is required, such as removal of a polyp, a treatment device is pushed over the device tail (supply line), as if over a guide-wire. While the therapeutic tool is being pushed on, the device is kept fully inflated to achieve anchoring to the end of the colon.

According to a variation of this embodiment, the treatment device is not pushed but is self-propelled by using inwardly directed inflation, such that it crawls up the guidewire, as shown in the embodiment of FIGS. 12A and 12B of the above mentioned PCT/I12006/000925.

The last few centimeters of the colon may be problematic to treat since the inflated device is located there, preventing access for treatment. According to a further embodiment of methods of use of the present invention, the device is stopped short of the end of the colon, and the treatment tool breaks through the tip of the working channel and has access to the distal end. Full colon coverage is thus obtained for the treatment tool Pigtail insertion is a frequent surgical procedure, such as is performed in ureteral bypass. According to a further preferred embodiment of the present invention, the pigtail, which is a simple pipe—curled at the ends, is equipped with a self-propelled device at one end. It will self-propel through the ureter and stay there, once disconnected from supply line. The principle applies not only for ureter bypass but for any applications requiring the placing of a bypass support. The supply channel of the self-propelled device described in the above mentioned PCT/I12006/000925 and in this application, can itself serve as bypass after disconnecting from the main fluid supply line.

The device can be combination of several different sized devices, where a smaller device will be used in the ureter, and the larger diameter one in the urethra. The two devices may preferably be inserted serially, and separated when the ureteral device is in place.

A number of different embodiments are now given by which the devices of the present invention may be manufactured. Referring now to FIGS. 17A to 17D, separator sections 160A, 160B, 160C are selectively covered by a soluble mask 161 at the regions where the balloons are to be formed, as shown in FIG. 17B. An alternative option is to cover all the outer area of sections 160 and selectively dissolve a negative image.

The whole device is then covered by elastic material 162 by molding or dipping techniques or any other elastomer manufacturing techniques as shown in FIG. 17C.

Finally, the mask material 161 is dissolved by injecting a solvent through channels 163 and the hollow balloons 164 are created as shown in FIG. 17D.

FIGS. 18A to 18D illustrate a further method of manufacture, wherein the hollow balloon area to be manufactured is made of a soluble material 151, and then covered with an elastic material 153. The soluble material is then dissolved through channels 152 and a hollow balloon 155 is created.

The soluble mask method can also be used for manufacturing annular double balloon systems, such as those described in FIG. 12 of the co-pending PCT/IL2006/000925. The procedure is shown in FIGS. 19A to 19D. The cylinder core 172 between the separator sections 170 is made from soluble material. The whole assembly is coated by an elastomer 173 inside and out, such as silicone or polyurethane. After curing the soluble core 172 is dissolved 174, leaving only the separator elements 170 with their orifices 175, and the annular balloon 173 over them. The double balloon system is then created, as shown in FIG. 19D.

Reference is now made to FIGS. 20A to 20D, which illustrate another preferred embodiment of the present invention, which enables the device to propagate in a flexible, slippery, or collapsible media. Use of this embodiment maintains the balloons 90A, 90B in contact with the lumen wall 1 most of the time. This embodiment is particularly important, for example, in colonoscopy, where the colon is normally in a collapsed and slippery configuration.

Figure 20A:
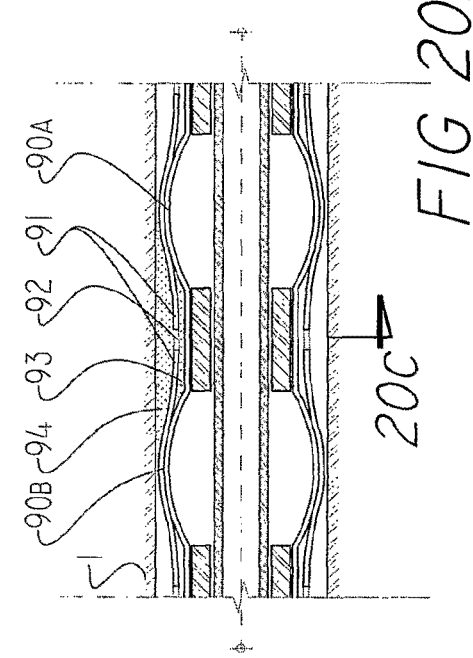
FIGS. 20A-20D illustrate another preferred embodiment of the present invention, which enables the device to propagate in a flexible, slippery, collapsible media, such as a colon, by maintaining firm contact between the balloons and the lumen wall.

A flexible membrane 91 connects neighboring balloons 90A, 90B, as shown in FIG. 20A. The membrane 91 may have small openings 92. When the balloons are deflated as in FIG. 20A, the flexible lumen 1 is generally collapsed onto the membrane 91, such that volumes 93 and 94 are closed volumes.

Figure 20B:
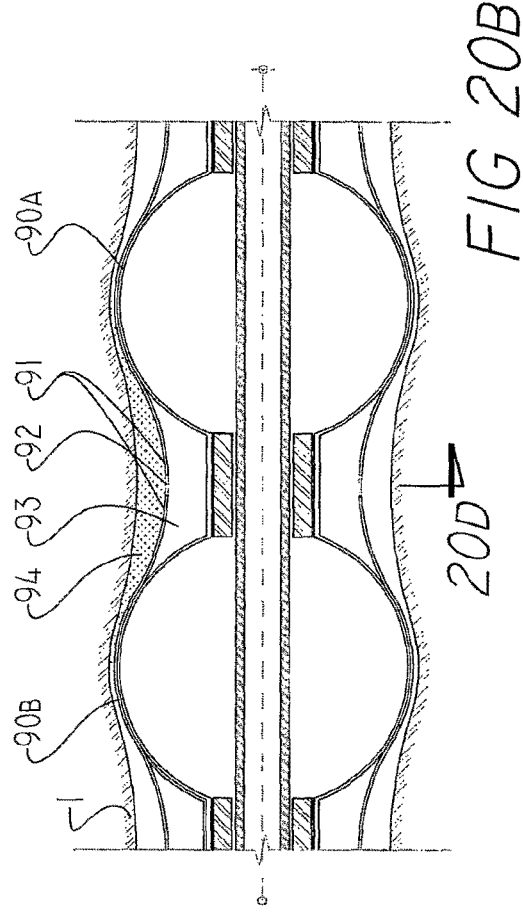

When the two adjacent balloons 90A, 90B, become inflated, as in FIG. 20B, the volumes 93 and 94 grow in volume but since they are closed volumes the pressure drops and the lumen 1 is pulled towards the membrane 91. By this means, the device achieves more friction with the lumen 1 which assists when propagating in slippery surrounding.

Figure 20C:
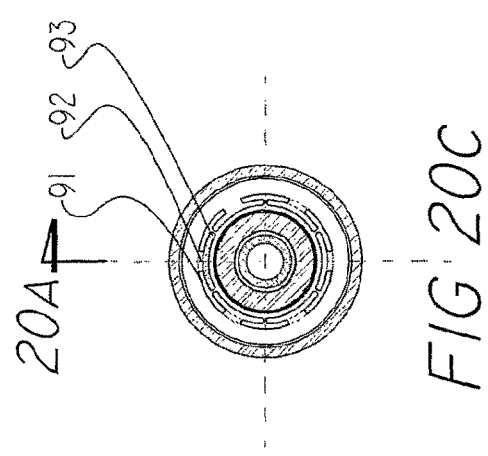
Figure 20D:
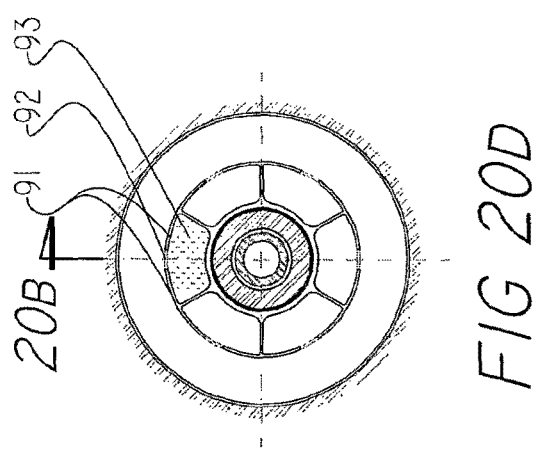

The membrane may be radially segmented as shown in cross sectional views, FIGS. 20C and 20D, which assists traction if the contact with the lumen 1 is so shaped that it only partially contacts the membrane 91 around its circumference. In such a case only some of the segments will be closed, since only some of the holes 92 will be in contact with the membrane, and hence closed off. According to this segmented construction, even if parts of the circumferential wall of the lumen do not touch the membrane 91, closure is still affected by other segments, and a good grip with the lumen wall is still ensured.

In a regular colonoscope, the CCD camera is preferably located at the tip. In this case the camera lens or front viewing window may become dirty from being pushed through and collecting any waste material in the colon. Furthermore, the colon wall is generally collapsed in its regular configuration, so that, in order to view the colon, the area under inspection should be inflated to open it up.

Reference is now made to FIGS. 21A and 21B, which illustrate another preferred embodiment of the present invention, which enables the device to view the lumen inner wall without getting contaminated. The camera 126 is located between two adjacent balloons, preferably close to the tip end, thus having a clear view of fully opened/stretched colon, as show in FIG. 21A. In addition to the balloon inflation tube 120, a channel 121 may preferably be provided for carrying optic fibers or electric leads for the optical or electronic camera. Channel 121 inside the balloons is preferably flexible, and so does not interfere with the device propagation sequence. Channel 121 can also be located outside of the device. The camera can be located facing outwards or inside the camera housing unit 125, and may be equipped with a light source—optical or electrical, illuminating the field of view 127.

According to a further preferred embodiment, wall cleaning capabilities may also preferably be mounted on the camera housing unit 125.

Reference is now made to FIG. 21B, which illustrates how the camera housing unit 125 can also preferably incorporate a therapeutic, steerable exit channel 129, for performing simple surgical procedures within the lumen. The channel can be mounted separately or in the same unit as the camera 126. The channel can have pitch, yaw and roll steering capabilities. It can be used for different devices inserted for inspection and/or therapy.

Reference is now made to FIG. 22, which illustrates another preferred embodiment of the present invention, in which a wall cleaning unit is located at the tip of the device, or between the balloons. Such an embodiment is useful in medical applications, such as colonoscopy or ureteroscopy for debris or stone removal or for cleaning. In FIG. 22, the inflated balloons system opens up the area and floating particles or particles 183 stuck to the lumen wall can be washed out by means of a stream of cleaning fluid supplied by incoming and outgoing double channels 180. Active or passive washers 184 move or vibrate the particles or fluids and they are washed out. The cleaning unit can be followed by a camera unit, such as that shown in FIG. 21A, so that after the surrounding walls have been cleaned using the present embodiment, the camera unit 126 can record clear pictures.

Finally, it is to be emphasized that although the various embodiments of FIGS. 3 to 22 have been generally described in relation to inflatable balloon devices where the inflation sequence is determined by the passive flow of fluid from one balloon to its neighboring balloon through a predetermined orifice, it is to be understood that the improvements and arrangements of these new embodiments can equally well be applied for use in inflatable balloon devices where the inflation sequence is generated by separate inflation lines, or by active control of fluid flow valves, such as are described in some of the prior art documents cited in the Background section of this application. The invention is thus not meant to be limited to passive sequentially inflatable balloon devices, but to be applicable to any sequentially inflatable balloon devices.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A self-propelled device for locomotion through a lumen, comprising:
   a set of serially arranged inflatable chambers, with a distal chamber at one end of said device, and a proximal chamber at the opposite end of said device, said inflatable chambers expanding in axial and radial directions when inflated;
   a fluid supply system connected only to said proximal one of said chambers;
   an axial channel running axially through said device, said channel being attached to a distal part of said device; and
   connecting passages providing fluid communication between pairs of adjacent chambers, said connecting passages being such that fluid from said supply system inflates said set of serially arranged inflatable chambers sequentially from said proximal inflatable chamber to said distal inflatable chamber, such that said device moves with the distal chamber leading.

2. A self-propelled device according to claim 1 and wherein attachment of said axial channel to a distal part of said device enables device to pulls said axial channel with it.

3. A self-propelled device according to claim 1 and wherein said axial channel is attached to either one of said distal chamber and said chamber immediately proximal to said distal chamber.

4. A self-propelled device according to claim 1, further comprising a sheath enclosing said axial channel, and wherein said fluid for inflating said chambers is supplied through said sheath.

5. A self-propelled device according to claim 1 and wherein said fluid for inflating said chambers is supplied through a separate supply tube.

6. A self-propelled device according to claim 4 and wherein said fluid supply system comprises a hermetically sealed rigid chamber, said chamber comprising:
an input port for inputting fluid to said rigid chamber;
an output port for outputting fluid to said sheath for inflating said inflatable chambers; and
a working channel port to which the proximal end of said axial channel is attached after traversing said rigid chamber in a path having a length of slack channel.

7. A self-propelled device according to claim 6 and wherein motion of said distal chamber of said device is operative to pull said axial channel, such that said length of slack channel shortens.

8. A self-propelled device according to claim 1 and wherein said inflatable chambers have the form of an annulus, said axial channel running through said annulus and outside of the inflatable volume of chambers, and wherein said fluid for inflating said chambers is supplied by a tube separate from said axial channel.

9. A self-propelled device according to claim 1 and wherein said axial channel is adapted to accommodate functional leads to either one of a viewing system and a therapeutic tool system carried at the distal end of said device.

10. A self-propelled device for locomotion through a lumen, comprising:
a set of serially arranged inflatable chambers having separator segments between adjacent chambers, said inflatable chambers expanding in axial and radial directions when inflated;
a fluid supply system for inflating said chambers sequentially;
connecting passages providing fluid communication between pairs of adjacent chambers, said connecting passages being such that fluid from said supply system inflates said set of serially arranged inflatable chambers sequentially from said chamber to which said fluid is supplied; and
stiffening elements inserted inside at least some of said chambers, said stiffening elements essentially filling the length of each of said chambers when uninflated, such that when said chambers are uninflated, said stiffening elements provide said device with axial rigidity between said separator elements associated with said chambers.

11. A self-propelled device according to claim 10 and further comprising an axial member disposed axially along said device, wherein said stiffening elements slide along said axial member as said chambers inflates.

12. A self-propelled device according to claim 10, and wherein at least one of said stiffening elements has a tubular form.

13. A self-propelled device according to claim 10 and wherein at least one of said stiffening elements is attached to a separator element.

14. A self-propelled device according to claim 10 and wherein at least one of said stiffening elements comprises one of the following (a), (b), and (c):
(a) two overlapping elements, each attached to a separator element at opposite ends of its chamber, one of said overlapping elements sliding within the other as said chamber inflates;
(b) a spring attached to said separator elements at opposite ends of said chamber, said spring having a closed length which essentially fills the length of said chamber when uninflated;
(c) an expandable cylindrical trellis structure attached to said separator elements at opposite ends of said chamber, said trellis structure having a closed length which essentially fills the length of said chamber when uninflated.

15. A self-propelled device according to claim 10 and wherein said chamber has an annular form, said device further comprising a central axial member running through the center of said annular chamber.

16. A self-propelled device for locomotion though a lumen, comprising:
A set of serially arranged inflatable chambers having separator segments between adjacent chambers fluidly isolated from said inflatable chambers, and said inflatable chambers expanding in axial and radial directions when inflated; and
a fluid supply system for inflating said chambers sequentially; and
connecting passages providing fluid communication between pairs of adjacent chambers, said connecting passages being such that fluid from said supply system inflates said set of serially arranged inflatable chambers sequentially from said chamber to which said fluid is supplied;
wherein at least one of said separator segments is flexible, such that part of said device in the vicinity of said at least one separator segment can negotiate a bend in said lumen by flexing of said at least one separator segment.

17. A self-propelled device according to claim 16 and wherein said at least one flexible separator segment has an interior that can be pressurized, such that the flexibility of said segment can be controlled in accordance with the inflation pressure of said segment.

18. A self-propelled device for locomotion through a lumen, comprising:
a set of serially arranged inflatable chambers, having at least a distal and a proximal chamber, said inflatable chambers expanding in axial and radial directions when inflated; and
a fluid supply system for inflating said chambers sequentially; and
connecting passages providing fluid communication between pairs of adjacent chambers, said connecting passages being such that fluid from said supply system inflates said set of serially arranged inflatable chambers sequentially from said chamber to which said fluid is supplied;
wherein said fluid supply system is connectable to said proximal chamber and to said distal chamber, such that said device can move in either direction in accordance with which of said chambers is supplied with fluid.

19. A self-propelled device according to claim 18 and wherein said fluid supply system is connectable to said proximal and distal chambers either by separate supply lines, or by means of a single supply line directed to one or the other of said proximal and distal chambers by means of a valve.

* * * * *